(12) United States Patent
Bunes et al.

(10) Patent No.: US 11,761,919 B2
(45) Date of Patent: Sep. 19, 2023

(54) QUANTITATIVE CHEMICAL SENSORS WITH RADIO FREQUENCY COMMUNICATION

(71) Applicants: University of Utah Research Foundation, Salt Lake City, UT (US); The Penn State Research Foundation, University Park, PA (US)

(72) Inventors: Benjamin R. Bunes, Salt Lake City, UT (US); Leonard Cardillo, Salt Lake City, UT (US); Douglas Later, Salt Lake City, UT (US); Ling Zang, Salt Lake City, UT (US); Douglas H. Werner, University Park, PA (US); Ronald Jenkins, University Park, PA (US); Micah D. Gregory, University Park, PA (US)

(73) Assignees: University of Utah Research Foundation, Salt Lake City, UT (US); The Penn State Research Foundation, University Park, PA (US)

( * ) Notice: Subject to any disclaimer, the term of this patent is extended or adjusted under 35 U.S.C. 154(b) by 671 days.

(21) Appl. No.: 16/510,742

(22) Filed: Jul. 12, 2019

(65) Prior Publication Data
US 2020/0018713 A1 Jan. 16, 2020

Related U.S. Application Data

(60) Provisional application No. 62/697,262, filed on Jul. 12, 2018.

(51) Int. Cl.
*G01N 27/12* (2006.01)
*G01R 23/02* (2006.01)
(Continued)

(52) U.S. Cl.
CPC ......... *G01N 27/122* (2013.01); *C07D 471/06* (2013.01); *G01N 27/127* (2013.01); *G01N 33/0057* (2013.01); *G01R 23/02* (2013.01)

(58) Field of Classification Search
CPC ... G01N 27/122; G01N 27/127; C07D 471/06
See application file for complete search history.

(56) References Cited

U.S. PATENT DOCUMENTS

| 5,600,325 A | 2/1997 | Whelan et al. |
| 6,525,695 B2 | 2/2003 | McKinzie, III |

(Continued)

FOREIGN PATENT DOCUMENTS

WO   WO 2004/013933 A1   2/2004

OTHER PUBLICATIONS

Anwar et al.; "Frequency Selective Surfaces: A Review." Applied Sciences; MDPI; Published Sep. 18, 2018; vol. 8, Issue 9; 46 Pages.
(Continued)

*Primary Examiner* — Alvaro E Fortich
(74) *Attorney, Agent, or Firm* — Thorpe North & Western

(57) ABSTRACT

A system for low power chemical sensing can include a voltage shift unit which receives a voltage signal from a chemical sensor unit. The voltage signal can be determined by a concentration of an analyte. The voltage shift unit can transform the voltage signal to an input voltage signal, and send the input voltage signal to a plurality of frequency selective surface (FSS) units of an FSS array. The FSS array can communicate a radio frequency (RF) signal in an Institute of Electrical and Electronics Engineers (IEEE) S band with a resonant frequency based on the input voltage to provide the concentration of the analyte.

22 Claims, 17 Drawing Sheets

(51) Int. Cl.
 C07D 471/06 (2006.01)
 G01N 33/00 (2006.01)

(56) References Cited

U.S. PATENT DOCUMENTS

| | | | |
|---|---|---|---|
| 6,774,867 B2 | 8/2004 | Diaz et al. | |
| 6,911,957 B2 | 6/2005 | Brown et al. | |
| 7,151,506 B2 | 12/2006 | Knowles et al. | |
| 7,190,325 B2 | 5/2007 | Nagy | |
| 7,256,753 B2 | 8/2007 | Werner et al. | |
| 7,408,147 B2 | 8/2008 | Blick et al. | |
| 7,679,563 B2 | 3/2010 | Werner et al. | |
| 7,826,504 B2 | 11/2010 | Chen et al. | |
| 8,486,708 B2 | 7/2013 | Zang et al. | |
| 8,633,866 B2 | 1/2014 | Sarabandi et al. | |
| 8,703,500 B2 | 4/2014 | Zang et al. | |
| 8,809,063 B2 | 8/2014 | Zang et al. | |
| 8,836,439 B2 | 9/2014 | O'Hara et al. | |
| 8,889,420 B2 | 11/2014 | Zang et al. | |
| 9,671,392 B2 | 6/2017 | Jeppsen et al. | |
| 10,096,905 B2 | 10/2018 | Cross et al. | |
| 10,151,720 B2 | 12/2018 | Wang et al. | |
| 10,164,326 B2 | 12/2018 | Urcia et al. | |
| 2005/0179614 A1* | 8/2005 | Nagy | H01Q 3/46 343/909 |
| 2008/0135614 A1 | 6/2008 | Werner et al. | |
| 2008/0224947 A1* | 9/2008 | Werner | H01Q 15/002 343/911 R |
| 2010/0097048 A1* | 4/2010 | Werner | H01Q 17/00 324/76.11 |
| 2012/0290268 A1* | 11/2012 | Bey | G01F 1/6845 702/189 |
| 2013/0130398 A1 | 5/2013 | Zang | |
| 2015/0118760 A1 | 4/2015 | Zang et al. | |
| 2017/0160252 A1 | 6/2017 | Zang et al. | |
| 2018/0053994 A1 | 2/2018 | Grando et al. | |
| 2018/0102592 A1 | 4/2018 | Frazier | |
| 2018/0201612 A1 | 7/2018 | Zang et al. | |

OTHER PUBLICATIONS

Debus et al.; "Frequency Selective Surfaces for High-Sensitivity Terahertz Sensors." 2007 Conference on Lasers and Electro-Optics (CLEO); IEEE; May 6-11, 2007; 2 Pages.

Eom et al.; "Frequency-Switchable Microfluidic CSRR-Loaded QMSIW Band-Pass Filter Using a Liquid Metal Alloy." Sensors; MDPI: Published Mar. 28, 2017; vol. 17, Issue 4; 10 Pages.

Lee et al.; "Design of Active Frequency Selective Surface with Curved Composite Structures and Tunable Frequency Response." International Journal of Antennas and Propagation; Hindawi; Published Nov. 9, 2017; vol. 2017; 10 Pages.

Martin et al.; "Application of RF-MEMS-Based Split Ring Resonators (SRRs) to the Implementations of Reconfigurable Stopband Filters: A Review." Sensors; MDPI; Published Dec. 2, 2014; vol. 14, Issue 12; pp. 22848-22863.

Salim et al.; "Simultaneous Detection of Two Chemicals Using a $TE_{20}$—Mode Substrate-Integrated Waveguide Resonator." Sensors; MDPI; Published Mar. 7, 2018; vol. 18, Issue 3; 18 Pages.

Wang et al.; "A frequency Tunable Double Band-Stop Resonator with Voltage Control by Varactor Diodes." Journal of Electromagentic Engineering and Science; Published Jul. 2016; vol. 16, Issue 3; pp. 159-163.

* cited by examiner

US 11,761,919 B2

QUANTITATIVE CHEMICAL SENSORS WITH RADIO FREQUENCY COMMUNICATION

RELATED APPLICATIONS

This application claims priority to U.S. Provisional Application No. 62/697,262, filed Jul. 12, 2018, which is incorporated herein by reference in its entirety for all purposes.

GOVERNMENT INTEREST

This invention was made with government support under Grant No. 1353637 awarded by National Science Foundation. The government has certain rights in the invention.

FIELD OF THE INVENTION

This invention relates to the field of vapor or gas detection specific nanomaterials and rf signal processing. Accordingly, the invention involves the fields of electrical engineering, nanotechnology, and electromagnetics.

BACKGROUND

Low power, remote wireless sensing is a field of increasing interest and growth within the field of electromagnetics. Developments in this area are motivated by a desire for a hands-off sensing approach. In these cases, direct user interaction with a provided sensor system in the weeks or months following deployment can be undesirable, unsafe, or even impractical. Under these circumstances, achieving a low total power consumption for the composite system can be critical to longevity and effectiveness. Low power sensors are in constant development by many companies for a wide range of applications. Large-scale sensor deployments, such as monitoring a train station or security checkpoint at an airport for chemical threats, can be costly. Much of the cost of a chemical sensor tends to be in the circuitry used to read the sensing element.

SUMMARY

A low power chemical sensing system can comprise a voltage shift unit, a frequency selective surface (FSS) array, and a radio frequency (RF) signal. The voltage shift unit can be configured to receive a voltage signal from a chemical sensor unit. The voltage signal varies based on a concentration of an analyte. The voltage shift unit can transform the sensor voltage signal into an input voltage signal, and send the input voltage signal to a plurality of FSS units of the FSS array.

The FSS array can comprise the plurality of FSS units. Each FSS unit can comprise a first resonator configured to receive a first voltage from the input voltage signal via a first bias line. Each FSS unit can also comprise a second resonator configured to receive a second voltage from the input voltage signal via a second bias line. Each FSS unit can comprise a variable capacitance unit coupled to the first resonator and the second resonator. The variable capacitance unit can be configured to convert a voltage bias from the first bias line and the second bias line to a capacitance. A varactor can vary the capacitance as a function of voltage to shift the resonance of the SRR. That allows the signal to be generated from the sensor. As an alternative, the varactor can be replaced by capacitors controlled by field effect transistors. Regardless, any such variable capacitance unit can be used.

The FSS array can be configured to produce an RF signal in an IEEE S band for communication to the RF receiver. The RF receiver can be configured to receive the RF signal in the S band. The RF receiver can be configured to identify a resonance frequency from a peak reflection magnitude from the RF signal. The RF receiver can be configured to determine the concentration of the analyte based on the resonant frequency.

There has thus been outlined, rather broadly, the more important features of the invention so that the detailed description thereof that follows may be better understood, and so that the present contribution to the art may be better appreciated. Other features of the present invention will become clearer from the following detailed description of the invention, taken with the accompanying drawings and claims, or may be learned by the practice of the invention.

BRIEF DESCRIPTION OF THE DRAWINGS

(FIG. 10A) An image of the spectra over the frequency range between 2.5 GHz and 3.5 GHz. (FIG. 10B) A zoomed in image of the spectra over the region of interest (2.8-3.1 GHz). (FIG. 11C) Summary of peak position at different applied voltages.

FIGS. 11A-C are sensor response data measured from the FSS, in accordance with one example of the present invention. (FIG. 11A) Sensor responses to three concentrations of ammonia under low illumination intensities. (FIG. 11B) Zoomed in spectra of the region of interest for three concentrations of ammonia under low illumination intensities. (FIG. 11C) Calibration curves of the sensor responses for peak position.

(FIG. 11D) Sensor responses to three concentrations of ammonia under high illumination intensities. (FIG. 11E) Zoomed in spectra of the region of interest for three concentrations of ammonia under high illumination intensities. (FIG. 11F) Calibration curves of the sensor responses for voltage transmitted to the FSS by the ATTiny microprocessor.

DETAILED DESCRIPTION

Figure 1:
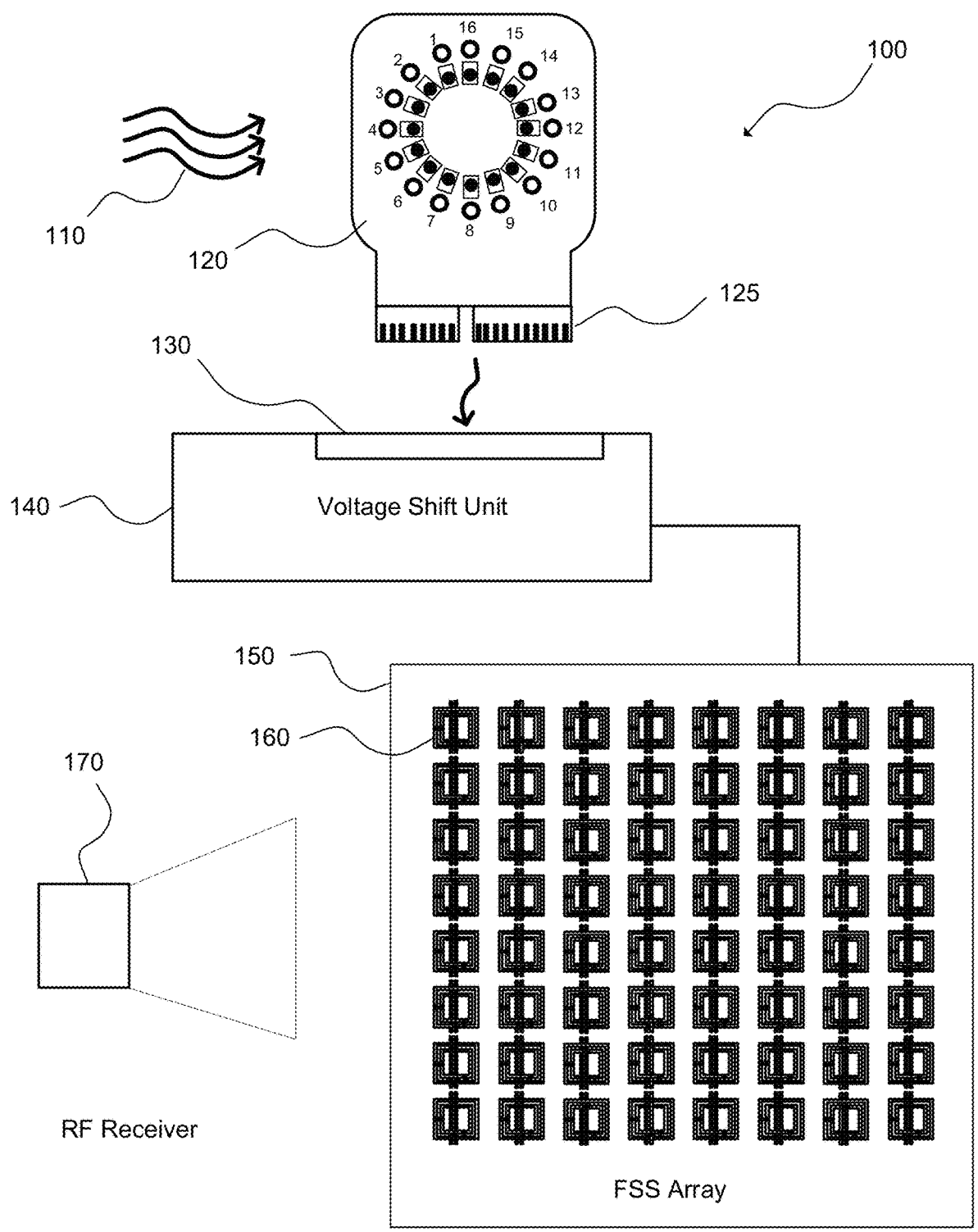
FIG. 1 is a graphical representation of a sensor system including a sensor card and control board configured to sense a toxic chemical, in accordance with one example of the present invention.

While these exemplary embodiments are described in sufficient detail to enable those skilled in the art to practice the invention, it should be understood that other embodiments may be realized and that various changes to the invention may be made without departing from the spirit and scope of the present invention. Thus, the following more detailed description of the embodiments of the present invention is not intended to limit the scope of the invention, as claimed, but is presented for purposes of illustration only and not limitation to describe the features and characteristics of the present invention, to set forth the best mode of operation of the invention, and to sufficiently enable one skilled in the art to practice the invention. Accordingly, the scope of the present invention is to be defined solely by the appended claims.

Definitions

In describing and claiming the present invention, the following terminology will be used.

The singular forms "a," "an," and "the" include plural referents unless the context clearly dictates otherwise. Thus, for example, reference to "a fiber" includes reference to one or more of such materials and reference to "exposing" refers to one or more such steps.

As used herein, "alkylene" refers to a saturated hydrocarbon having two valencies, i.e. for bonding with adjacent groups. Non-limiting examples of alkylenes include —CH—, —CH$_2$—, —C$_2$H$_4$—, —C$_3$H$_6$—, etc. This is in contrast to "alkyl" groups which are similar but have a single valency and include at least one CH$_3$ end group.

As used herein with respect to an identified property or circumstance, "substantially" refers to a degree of deviation that is sufficiently small so as to not measurably detract from the identified property or circumstance. The exact degree of deviation allowable may in some cases depend on the specific context.

As used herein, "adjacent" refers to the proximity of two structures or elements. Particularly, elements that are identified as being "adjacent" may be either abutting or connected. Such elements may also be near or close to each other without necessarily contacting each other. The exact degree of proximity may in some cases depend on the specific context.

As used herein, the term "about" is used to provide flexibility and imprecision associated with a given term, metric or value. The degree of flexibility for a particular variable can be readily determined by one skilled in the art. However, unless otherwise enunciated, the term "about" generally connotes flexibility of less than 2%, and most often less than 1%, and in some cases less than 0.01%.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

As used herein, the term "at least one of" is intended to be synonymous with "one or more of." For example, "at least one of A, B and C" explicitly includes only A, only B, only C, and combinations of each.

Concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a numerical range of about 1 to about 4.5 should be interpreted to include not only the explicitly recited limits of 1 to about 4.5, but also to include individual numerals such as 2, 3, 4, and sub-ranges such as 1 to 3, 2 to 4, etc. The same principle applies to ranges reciting only one numerical value, such as "less than about 4.5," which should be interpreted to include all of the above-recited values and ranges. Further, such an interpretation should apply regardless of the breadth of the range or the characteristic being described.

Any steps recited in any method or process claims may be executed in any order and are not limited to the order presented in the claims. Means-plus-function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus function are expressly recited in the description herein. Accordingly, the scope of the invention should be determined solely by the appended claims and their legal equivalents, rather than by the descriptions and examples given herein.

Quantitative Chemical Sensors with Radio Frequency Communication

An initial overview of invention embodiments is provided below and specific embodiments are then described in further detail. This initial summary is intended to aid readers in understanding the technological concepts more quickly, but is not intended to identify key or essential features thereof, nor is it intended to limit the scope of the claimed subject matter.

As illustrated in FIG. 1, chemical sensing system 100 can comprise a voltage shift unit 140 configured to receive a voltage signal from a chemical sensor unit 120. The voltage signal can be determined by a concentration of an analyte 110. The voltage shift unit 140 can be configured to transform the voltage signal to an input voltage signal. The voltage shift unit 140 can be configured to send the input voltage signal to a plurality of frequency selective surface (FSS) units 160 of an FSS array 150. The FSS array 150 can be configured to communicate a radio frequency (RF) signal in an Institute of Electrical and Electronics Engineers (IEEE) S band with a resonant frequency based on the input voltage to provide the concentration of the analyte 110. Although a microcontroller can be used as the voltage shift unit 140, any unit which shifts voltage into a suitable voltage range for the varactor or other variable capacitance unit can be used. Alternatively, the voltage signal from the chemical sensor unit 120 can be communicated through at least one amplifier and at least one level shifter to provide the varactor (or other variable capacitance unit) with the input voltage signal. In this case a microcontroller can be omitted. In another alternative, the voltage shift unit can be provided by applying an increased bias voltage to the nanofibers of the chemical sensor.

A complementary method for low power chemical sensing can include receiving, at a microcontroller 140 from a chemical sensor unit 120, a voltage signal determined by a concentration of an analyte 110. The method can further include sending, at the microcontroller 140 to a plurality of FSS units 160 of an FSS array 150, an input voltage signal determined using the voltage signal from the chemical sensor unit 120. The method can further include communicating, from the FSS array 150 to an RF receiver 170, an RF signal in a IEEE S band with a resonant frequency. The RF signal can be determined using the input voltage signal. The method can further include determining, at the RF receiver 170, the concentration of the analyte 110 based on the resonant frequency.

A sensor based on organic nanofibers can capture chemicals in the air and change conductivity in response. Compared to other chemical sensors, the organic nanofibers can be more sensitive and selective. Additionally, organic nanofibers can consume low amounts of power and can be paired with radio frequency technology. Deployment costs can be greatly reduced by operating all sensors wirelessly from a single base station.

Chemical sensors used for monitoring can be housed in a handheld or mountable instrument. However, handheld instruments may only operate for 8 hours or less before their batteries are depleted. Mountable instruments may only use an external power source, which can limit their portability and placement. The sensor system in this disclosure can use low power circuitry configured to operate continuously for one or more months on two coin-sized batteries (e.g., CR2032 batteries).

Other chemical sensors based on RF platforms can signal a change in sensor response based on the height of a reflectance spectrum. However, the height of the reflectance spectrum can be affected by the distance and direction between the sensor and the receiver. The varactor in this disclosure can be configured to shift the frequency of the reflectance band. The frequency of the reflectance band can be minimally impacted by the distance and direction between the sensor and the receiver. The frequency shift can be sufficient to indicate that a chemical is present at a hazardous level, such as a permissible exposure level (PEL) or immediately dangerous to health or life (IDLH).

The varactor can be controlled by a low-power circuit (i.e. less than about 2 mW). A microcontroller can read the sensor by receiving the sensor voltage signal and adjust the varactor to a predetermined value to select a frequency. This type of platform can enhance performance to enable the sensor to adapt to various applications. For example, in health and safety monitoring, the permissible exposure limit (PEL) and immediately dangerous to life or health (IDLH) limit can be used. For a sensor with a linear response to chemical concentration, the PEL limit may be near the detection limit if the width of the reflectance bands of the range is not large enough to include the IDLH limit. By using a varactor, the response of an RF antenna may not be linearly proportional to concentration. A safe reading below the PEL limit can be set to a baseline and the IDLH limit can be set to be near the maximum allowable with the PEL limit in between the safe reading and the IDLH limit. In this example, the safe readings, PEL limit, and IDLH limit can be resolved at a higher resolution that in systems without active components. Of course, alternative limits can be set for specific applications (e.g. industrially economic limits, likely explosive residue presence, etc). Thresholds could also be set to detect thresholds that affect industrial processes.

The system 100 for low power chemical sensing can generally comprise a microcontroller 140, a frequency selective surface (FSS) array 150, and an RF receiver 170. The microcontroller 140 can be configured to receive a sensor voltage signal from a chemical sensor unit 120, as illustrated in FIG. 1. The voltage signal can be determined by a concentration of an analyte 110.

The analyte can include chemical compounds that can be detected for health and safety applications, intelligence and law enforcement applications, or large-scale screening of an area. For health and safety applications, the environment can change quickly (especially with respect to mining). With traditional handheld sensors, a person may only obtain a measurement by entering a dangerous or potentially dangerous area. The sensors disclosed herein can be interrogated wirelessly without sending a person into a dangerous or potentially dangerous environment.

For intelligence and law enforcement applications, chemical detection can be used to identify clandestine manufacturing products, such as explosives (e.g., triacetonetriperoxide, ammonium nitrate), narcotics (e.g., methamphetamine), or chemical warfare agents (e.g., sarin, Novichok agents). These sensor systems can also be deployed widely because the components can be inexpensive and disposable.

For large-scale screening of an area for a potential threat, some prior art instruments can be expensive (e.g., $20,000 to $100,000) which tends to limit the number of instruments that can be deployed. These systems are typically installed in small numbers and trained staff collect and deliver samples to the instruments. The sensors disclosed herein can be lower cost which can allow for more widespread monitoring. In one example, the instrument (e.g., a network analyzer or RF reader) may not physically contain the chemical sensors and can be configured to interrogate multiple elements (e.g. signals from multiple different chemical sensors and/or FSS arrays). As a result, a large number of sensors can be deployed at a low-cost and read by a single RF reader. The increased number of sensors can also enhance area coverage.

Figure 2:
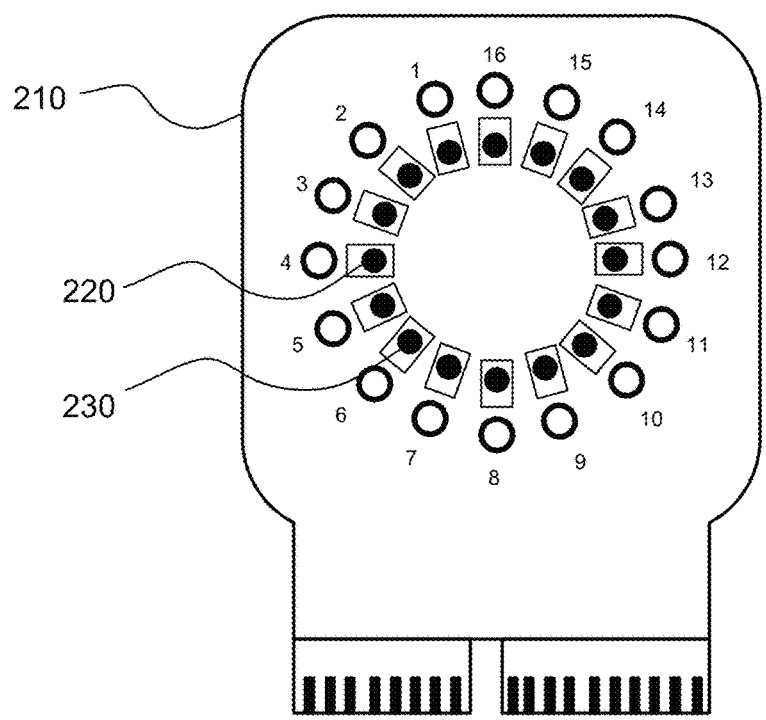
FIG. 2 is a graphical representation of a sensor card including a plurality of nanofiber sensors, in accordance with one example of the present invention.

The chemical sensor unit 210 (e.g. element 120 in FIG. 1) can comprise a plurality of nanofiber sensors 220, 230, as illustrated in FIG. 2. Such chemical sensor units can include one to several hundred individual nanofiber sensors, but most often from 4 to 100 sensors. In some cases, each nanofiber sensor can be formed of common nanofibers and can be configured to detect a common analyte. Such multiple common analyte sensors can provide additional data points and improved analyte detection accuracy. However, in some cases, the chemical sensor unit can include a plurality of nanofiber sensor types (e.g. configured to detect different analytes). Each sensor type can have one or more chemical sensors with a common analyte sensitivity. Such composite sensor units can be operated so as to detect individual analytes one at a time or simultaneously (e.g. operate sequentially in time or contemporaneously). Other non-limiting examples of chemical sensors can include electrochemical cells, metal oxides, microelectromechanical systems, carbon nanotubes, inorganic nanowires, graphene, two-dimensional dichalcogenides, and metalorganic frameworks.

Regardless, the nanofiber sensors 220, 230 can be configured to change conductivity based on the concentration of the analyte. The nanofiber sensor 220, 230 can be activated by exposure to a threshold illumination. In another example, the nanofiber sensors 220, 230 may be activated without exposure to a threshold illumination. The nanofiber sensors 220, 230 can include a filter to increase the selectivity of the nanofiber sensors. The nanofiber sensor 220, 230 can be comprised of nanofibers. In some cases the nanofibers can be deposited between a pair of electrodes, while in other cases changes in fluorescence can be detected and converted to an electrical signal. Although any analyte responsive nanofibers can be used, non-limiting exemplary nanofibers are described in U.S. Pat. Nos. 8,486,708; 8,703,500; 8,809,063; 8,889,420; and 10,151,720; and U.S. Patent Application Publication Nos. 2013/0130398; 2015/0118760; 2017/0160252; and 2018/0201612 which are all incorporated herein by reference. Of particular interest are nanofibers formed of perylene tetracarboxylic diimide molecules as described in the above patents and patent applications, with particular attention to those described in U.S. Patent Application Publication Nos. 2017/0160252 and 2018/0201612.

The microcontroller 140 can be further configured to transform the sensor voltage signal that has been determined by a concentration of an analyte 110 to an input voltage signal. For example, a sensor 120 (e.g., VAP-025) can be exposed to various concentrations of ammonia. The varying concentrations of ammonia exposure can produce varying changes in conductivity at the sensor 120. These changes in conductivity at the sensor 120 can produce varying amounts of current at the sensor 120. The varying current amounts can be converted to a voltage that can often range between 0 volts (V) and 2 V (e.g., the voltage signal).

The voltage signal from the sensor 120 can be digitized using an analog-to-digital converter (ADC) (e.g., a 20-bit delta-sigma analog-to-digital converter). Serial signals from the ADC can be input to a control card 130 via an interface 125. A low power processor (e.g., an ATTiny microprocessor) on the control card 130 can read the voltage from the ADC and output pulse width modulated (PWM) signals to a charge storage capacitor and filter. The voltage from the ADC can be multiplied to produce a wider voltage range (e.g., 0 V to 10 V) (e.g., the input voltage signal).

The input voltage signal can then be sent to a plurality of frequency selective surface (FSS) units 160 of an FSS array 150. The number of FSS units 160 in the FSS array 150 can be selected to produce a radio frequency (RF) signal with a signal-to-noise ratio (SNR) greater than a selected threshold. In one example, the number of FSS units 160 can be about 400 units. In another example, the number of units can be in a range from 16 to 10,000.

Figure 3:
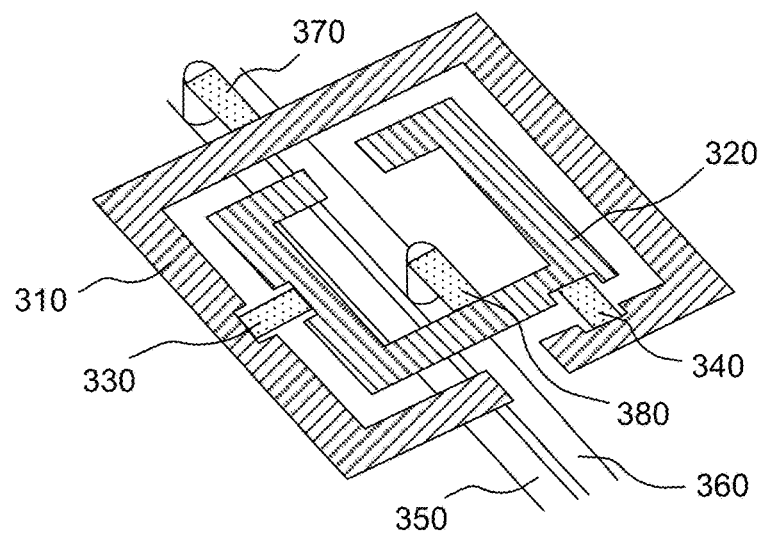
FIG. 3 is a graphical representation of two nested split-ring resonators coupled to a varactor diode and a capacitor, in accordance with one example of the present invention.
Figure 4:
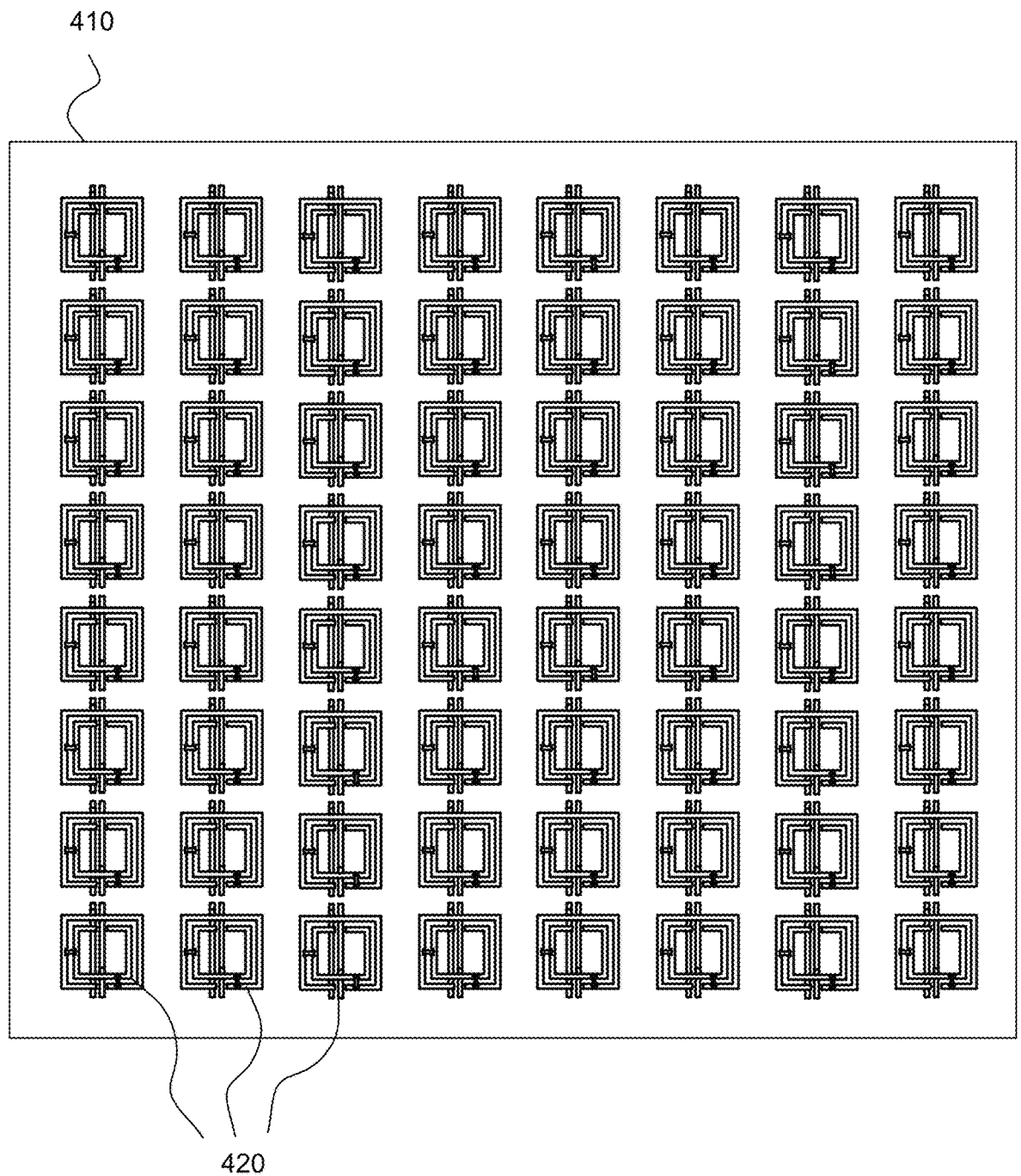
FIG. 4 is a graphical representation of a frequency selective surface (FSS) array, in accordance with one example of the present invention.

As illustrated in FIG. 3, each FSS unit of the FSS array can comprise: a first resonator 310, a second resonator 320, and a varactor 330. In one example, at least one of the first resonator 310 and the second resonator 320 can include a tunable resonator such as at least one of: transmission line and coaxial, dielectric, crystal, ceramic, surface acoustic wave (SAW), bulk acoustic wave (BAW), yttrium iron garnet (YIG) resonators, and the like. In one example, at least one of the first resonator 310 and the second resonator 320 can include a split ring resonator (SRR) such as at least one of: a 1-D split-ring structure, a symmetrical ring structure, an omega structure, a coupled "S" shaped structure, a spiral resonator, a broadside-coupled split ring resonator, two-layer multi spiral resonator, broad-side coupled spiral resonator with four turns, a complementary split ring resonator, an open split ring resonator, and an open complementary split ring resonator.

The first resonator 310 can comprise a first nested split-ring resonator (SRR) configured to receive a first voltage from the input voltage signal via a first bias line 350. Biasing can be achieved through a copper trace that trace between unit cells. The copper trace can be positioned perpendicular to the polarization of the FSS array. This orientation can be selected to minimize the effect of the bias line on the reflection response of the FSS array. The first bias line 350 can be brought up through the substrate (e.g., Taconic TLY with a relative permittivity of approximately 2.2) and connected via one or more choke inductors 370 to the first nested SRR 310. A via can carry the first bias voltage from the back plane to the first nested SRR 310.

The one or more choke inductors 370 can be configured to isolate the first bias line 350 over an operating bandwidth. In one example, the operating bandwidth can include a frequency range in an Institute of Electrical and Electronics Engineers (IEEE) short wave (S) band corresponding to a frequency range of about 2 gigahertz (GHz) to 4 GHz. In another example, the operating bandwidth can include a frequency range within the IEEE S band (e.g., about 2.7 GHz to 3.2 GHz). In another example, the operating bandwidth can include a frequency range within the IEEE S band of about 2.80 GHz to about 3.05 GHz.

The second resonator 320 can comprise a second nested split-ring resonator (SRR) configured to receive a second voltage from the input voltage signal via a second bias line 360. Biasing can be achieved through a conductive (e.g., copper) trace that run between unit cells. The copper trace can be positioned perpendicular to the polarization of the FSS array. This orientation can be selected to minimize the effect of the bias line 360 on the reflection response of the FSS array. In an FSS array, the bias lines 350 and 360 can be electrically common throughout the array, unless different RF transmission zones are desired (e.g. for simultaneous analyte detection from multiple different chemical sensors).

The second bias line 360 can be brought up through the substrate (e.g., Taconic TLY with a relative permittivity of approximately 2.2) and connected via one or more choke inductors 380 to the second nested SRR 320. A via can carry the second bias voltage from the back plane to the second nested SRR 320. The one or more choke inductors 380 can be configured to isolate the second bias line 360 over the operating bandwidth, as described in the preceding.

The varactor 330 (e.g., a varactor diode) can be coupled to the first resonator 310 and the second resonator 320. The varactor 330 can be configured to convert a voltage from a first bias and a voltage from a second bias to a capacitance. In one example, the varactor 330 can be coupled to a first nested split ring resonator 310 and a second nested split ring resonator 320. The varactor 330 can convert the voltage bias from the first bias line 350 and the second voltage bias from the second bias line 360 into a capacitance. A capacitor 340 can be coupled to the first resonator 310 and the second resonator 320. The capacitor shifts the resonant frequency so as to align signal information from the chemical sensors to the corresponding receiver.

Based on the input voltage signal, the capacitance from the varactor 330 can be tuned to produce an RF signal in an Institute of Electrical and Electronics Engineers (IEEE) S band for communication to an RF receiver. The IEEE S band can include a frequency range between about 2 GHz and 4 GHz. The capacitance from the varactor 330 can be tuned to a value at each of the unit cells 420 of the FSS array 410 to produce an RF signal within a frequency band within the frequency range between 2 GHz and 4 GHz. In one example, the operating bandwidth can include a frequency range between 2.80 gigahertz (GHz) and 3.05 GHz. The FSS array 410 can be configured to produce radio detection and ranging (RADAR) identifiable reflection band tuning.

In one example, the microcontroller 140 can be further configured to select a value of the input voltage signal to determine a resonant frequency. The resonant frequency can be a peak reflection magnitude that can be identified from the RF signal in the operating frequency range of the IEEE S band. The peak reflection magnitude can have a reflection magnitude of greater than −10 dB. The voltage values within the operating range can have a high Q-factor to enable a continuous usable tuning range.

In one example, the microcontroller 140 can be further configured to select the value of the input voltage signal based on a mapping between the concentration of an analyte 110 and the resonant frequency. In one example, the microcontroller 140 can be configured to: identify a first threshold value for the voltage signal received from the chemical sensor unit, and identify a second threshold value for the voltage signal received from the chemical sensor unit 120, 210. When the value for the voltage signal is between the first threshold value and the second threshold value, the concentration of the analyte 110 can be in a permissible exposure limit (PEL) range. When the value for the voltage signal is higher than the second threshold value, the concentration of the analyte 110 can be in an immediately dangerous to life or health (IDLH) range.

In one specific example, the analyte 110 can include ammonia. The permissible exposure limit for ammonia can be 50 parts per million (ppm) and the immediately dangerous to life and health limit for ammonia can be 300 ppm. In one example, when measured in the presence of a high light intensity (e.g., 160,000 LUX at the sensor), the voltage difference at the sensors could be: 1.5 V for an ammonia concentration of approximately 0 ppm; 1.95 V for an ammonia concentration of approximately 9 ppm; and 10.1 V for an ammonia concentration of approximately 300 ppm. In this example, the ammonia concentration below the PEL threshold could be resolved, and the ammonia concentration near the IDLH threshold could be resolved.

A voltage signal range between 0 V and 12 V can correspond to a concentration range including a concentration that is (a) below the PEL limit, (b) above the PEL limit but below the IDLH limit, and (c) above the IDLH limit. The voltage signal between 0V and 12V can be mapped to specific resonant frequencies. These resonant frequencies can be identified to determine the concentration of the analyte 110.

Figure 5:
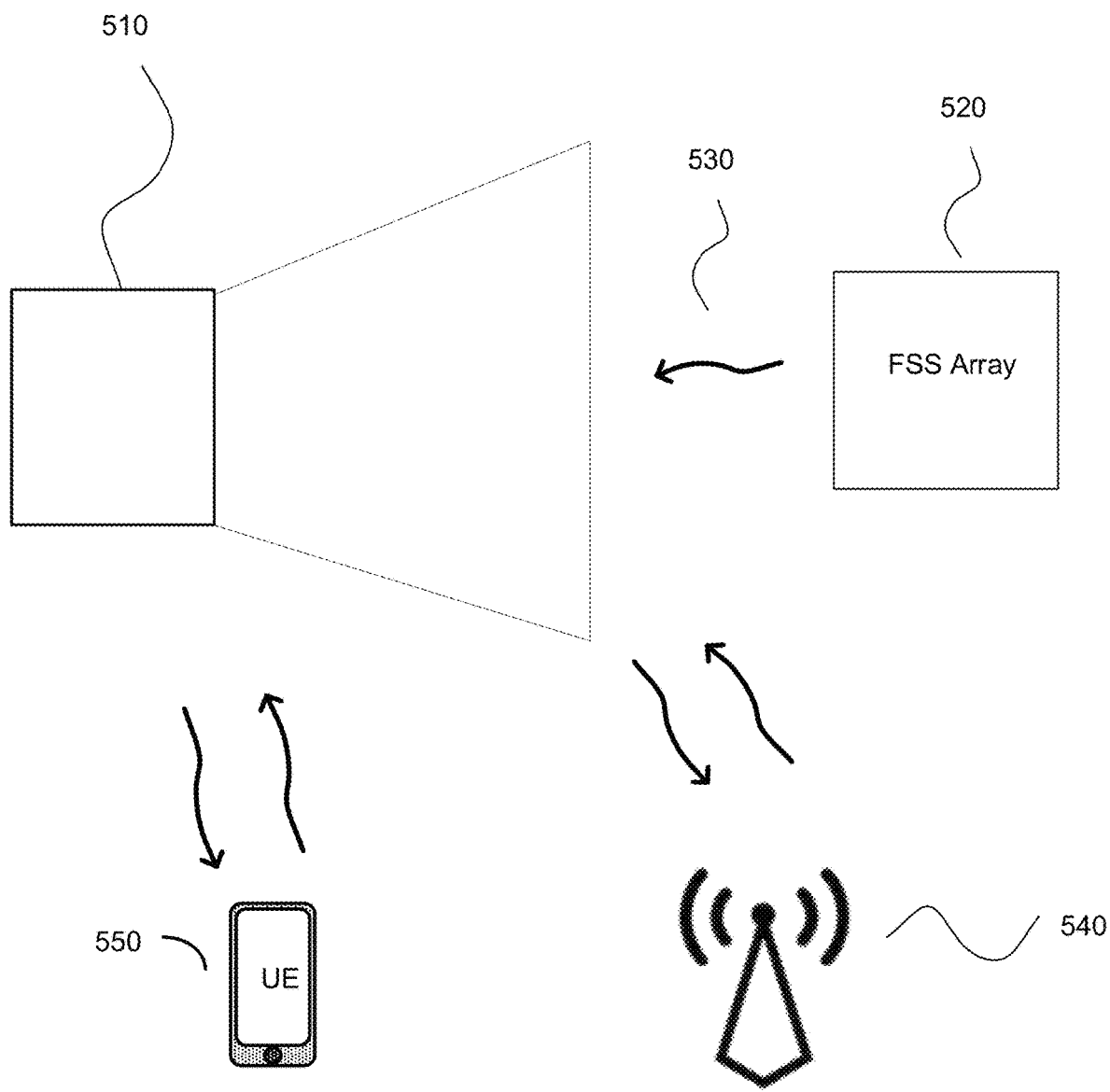
FIG. 5 is a graphical representation of a radio frequency (RF) receiver, in accordance with one example of the present invention.

The RF receiver 510 (e.g., a pyramidal antenna design), as illustrated in FIG. 5, can be configured to receive the RF signal 530 that is communicated by the FSS array 520. The RF signal 530 communicated from the FSS array 520 can include the S band frequency range. The RF receiver 510 can be configured to identify a resonant frequency from the peak reflection magnitude from the RF signal 530. The peak reflection magnitude can include a reflection magnitude of greater than −10 dB. The frequency associated with the peak reflection magnitude can be the resonant frequency. The RF receiver 510 can be configured to determine the concentration of the analyte 110 based on the resonant frequency. Based on the determined concentration of the analyte 110, the RF receiver 510 can be configured to identify that the concentration of the analyte 110 is in a permissible exposure limit range or an immediately dangerous to life or health range.

In another example, the system for low power sensing can further include a control board configured to be connected to a power source. The power source can be configured to power at least one of the chemical sensor unit 120, the microcontroller 140, and the FSS array 150. The power source can be configured to provide a total current of less than 250 microamperes ($\mu$A). In one example, the power source can comprise two lithium coin batteries (e.g. CR2032) that can provide for continuous operation for longer than a month.

In another example, the system for low power sensing can further include a base station 540, such as a network analyzer (e.g., an Agilent E5071C network analyzer with 100 kilohertz (kHz) to 8.5 gigahertz (GHz) bandwidth). The network analyzer can be a portable network analyzer or a stationary network analyzer. The network analyzer can be configured to read the output of the RF receiver 510 and transmit information to the RF receiver 510. In another example, a user equipment (UE) 550 can be configured to read the output of the RF receiver 510 and transmit information to the RF receiver 510. The UE 550 may replace the functionality of the base station 540. The base station 540, the UE 550, or both can be configured to read the output of the RF receiver 510.

In another example, the system for low power sensing can further include a chemical sensor unit configured to sense analyte concentrations for a plurality of distinct analytes. The concentrations of distinct analytes can be communicated from the FSS array using time-based monitoring. In one example, the FSS array can be configured to communicate a first concentration of a first analyte in a first time period, a second concentration of a second analyte in a second time period, and so forth for any additional analytes.

Figure 6:
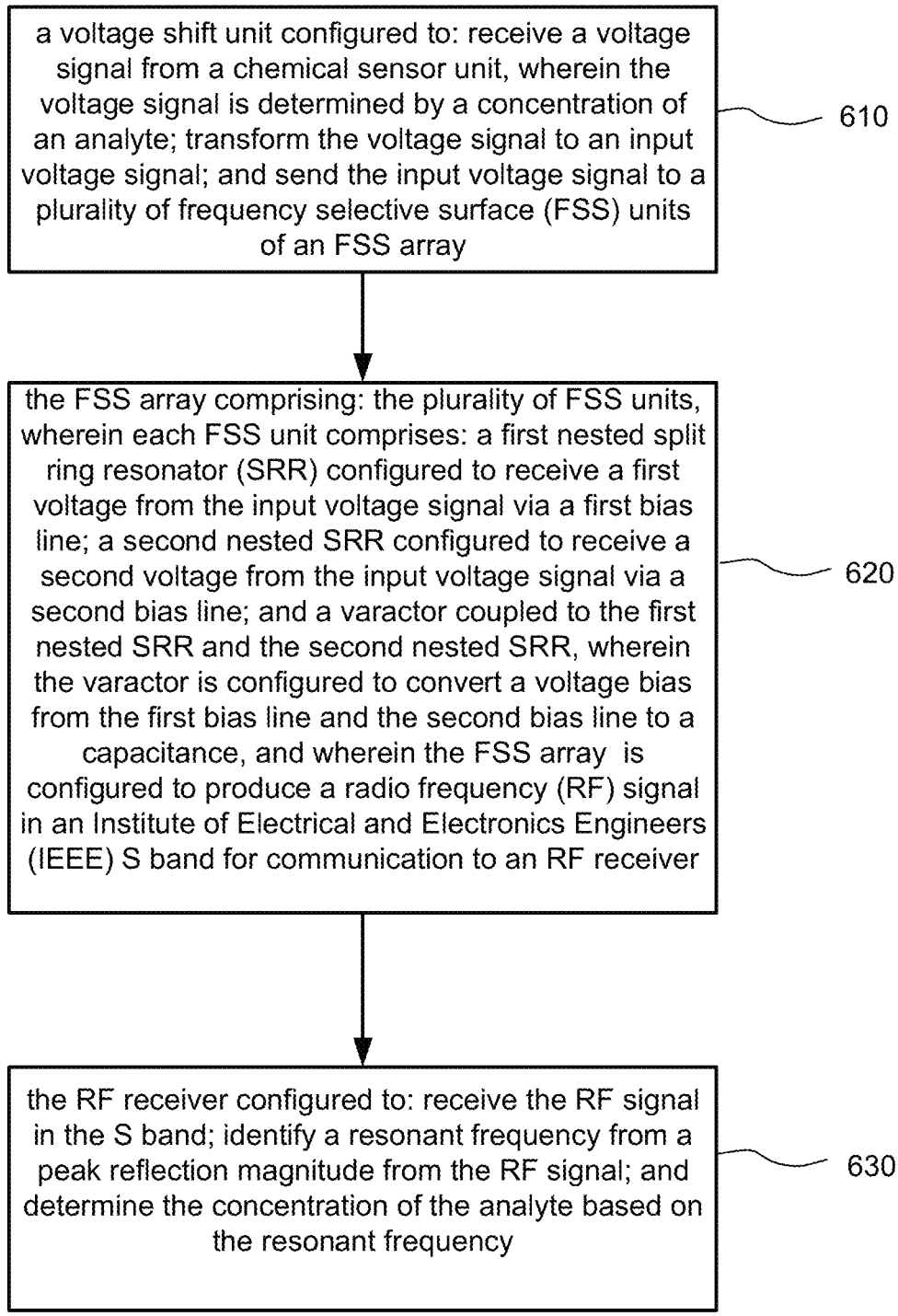
FIG. 6 is a flowchart depicting a system for low power chemical sensing, in accordance with one example of the present invention.

Another example provides functionality of a system for low power chemical sensing, as shown in FIG. 6. The system can comprise a microcontroller configured to: receive a voltage signal from a chemical sensor unit, wherein the voltage signal is determined by a concentration of an analyte; transform the voltage signal to an input voltage signal; and send the input voltage signal to a plurality of frequency selective surface (FSS) units of an FSS array, as in block 610. The system can comprise the FSS array comprising: the plurality of FSS units, wherein each FSS unit comprises: a first nested split ring resonator (SRR) configured to receive a first voltage from the input voltage signal via a first bias line; a second nested SRR configured to receive a second voltage from the input voltage signal via a second bias line; and a varactor coupled to the first nested SRR and the second nested SRR, wherein the varactor is configured to convert a voltage bias from the first bias line and the second bias line to a capacitance, and wherein the FSS array is configured to produce a radio frequency (RF) signal in an Institute of Electrical and Electronics Engineers (IEEE) S band for communication to an RF receiver, as in block 620. The system can comprise the RF receiver configured to: receive the RF signal in the S band; identify a resonant frequency from a peak reflection magnitude from the RF signal; and determine the concentration of the analyte based on the resonant frequency, as in block 630.

Figure 7:
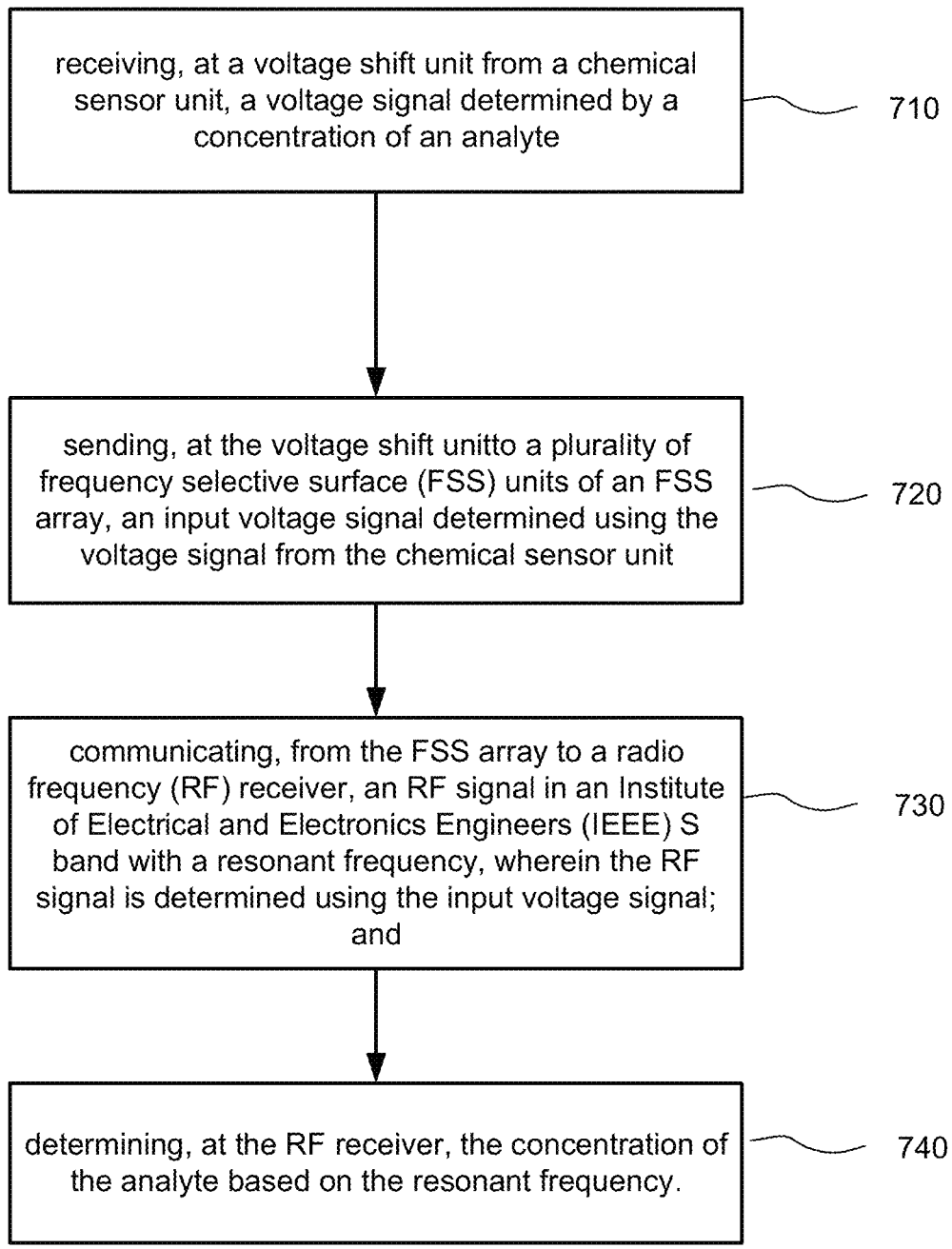
FIG. 7 is a flowchart depicting a method for low power chemical sensing, in accordance with one example of the present invention.

Another example provides a method for low power chemical sensing, as shown in FIG. 7. The method can comprise receiving, at a microcontroller from a chemical sensor unit, a voltage signal determined by a concentration of an analyte, as in block 710. The method can comprise sending, at the microcontroller to a plurality of frequency selective surface (FSS) units of an FSS array, an input voltage signal determined using the voltage signal from the chemical sensor unit, as in block 720. The method can comprise communicating, from the FSS array to a radio frequency (RF) receiver, an RF signal in an Institute of Electrical and Electronics Engineers (IEEE) S band with a resonant frequency, wherein the RF signal is determined using the input voltage signal, as in block 730. The method can comprise determining, at the RF receiver, the concentration of the analyte based on the resonant frequency, as in block 740.

Figure 8:
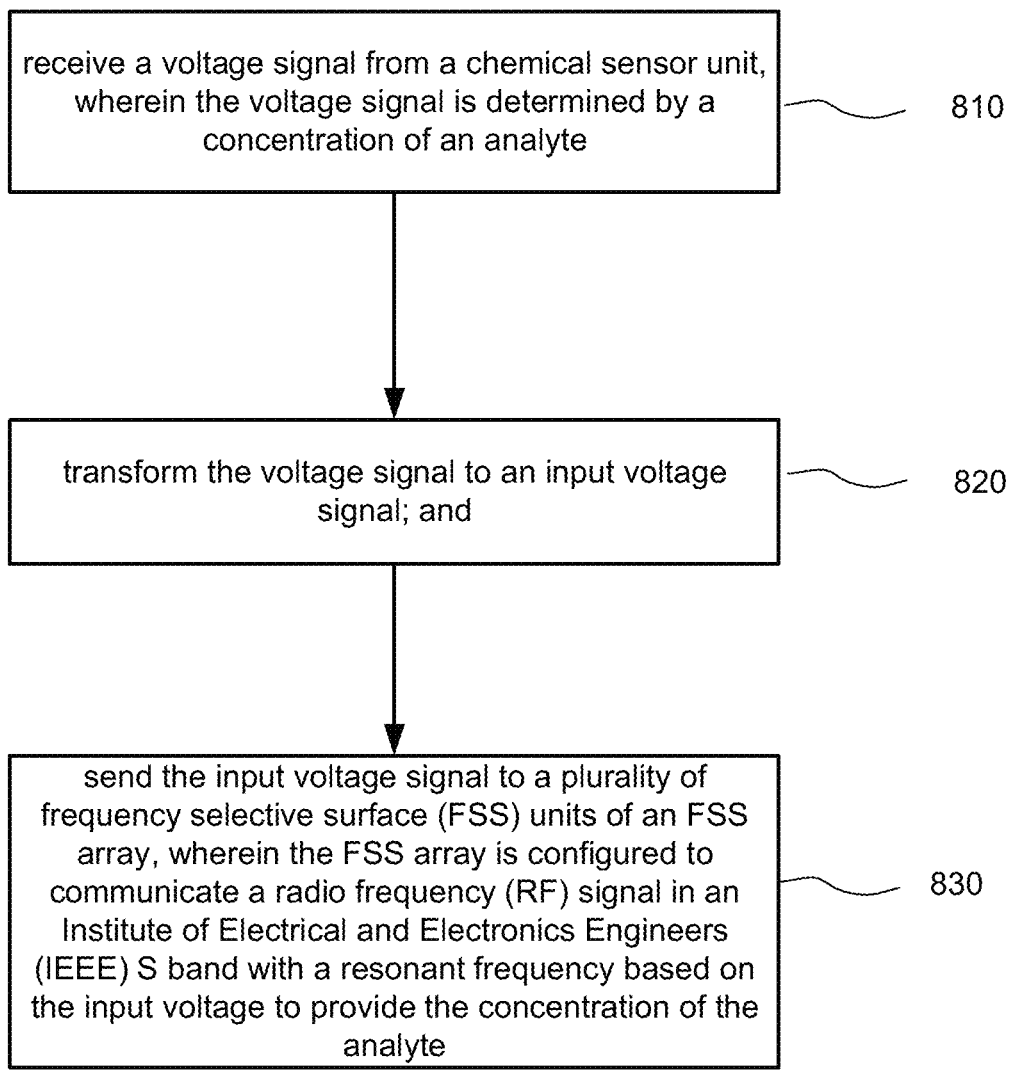
FIG. 8 is a flowchart depicting an apparatus for low power chemical sensing, in accordance with one example of the present invention.
Figure 9:
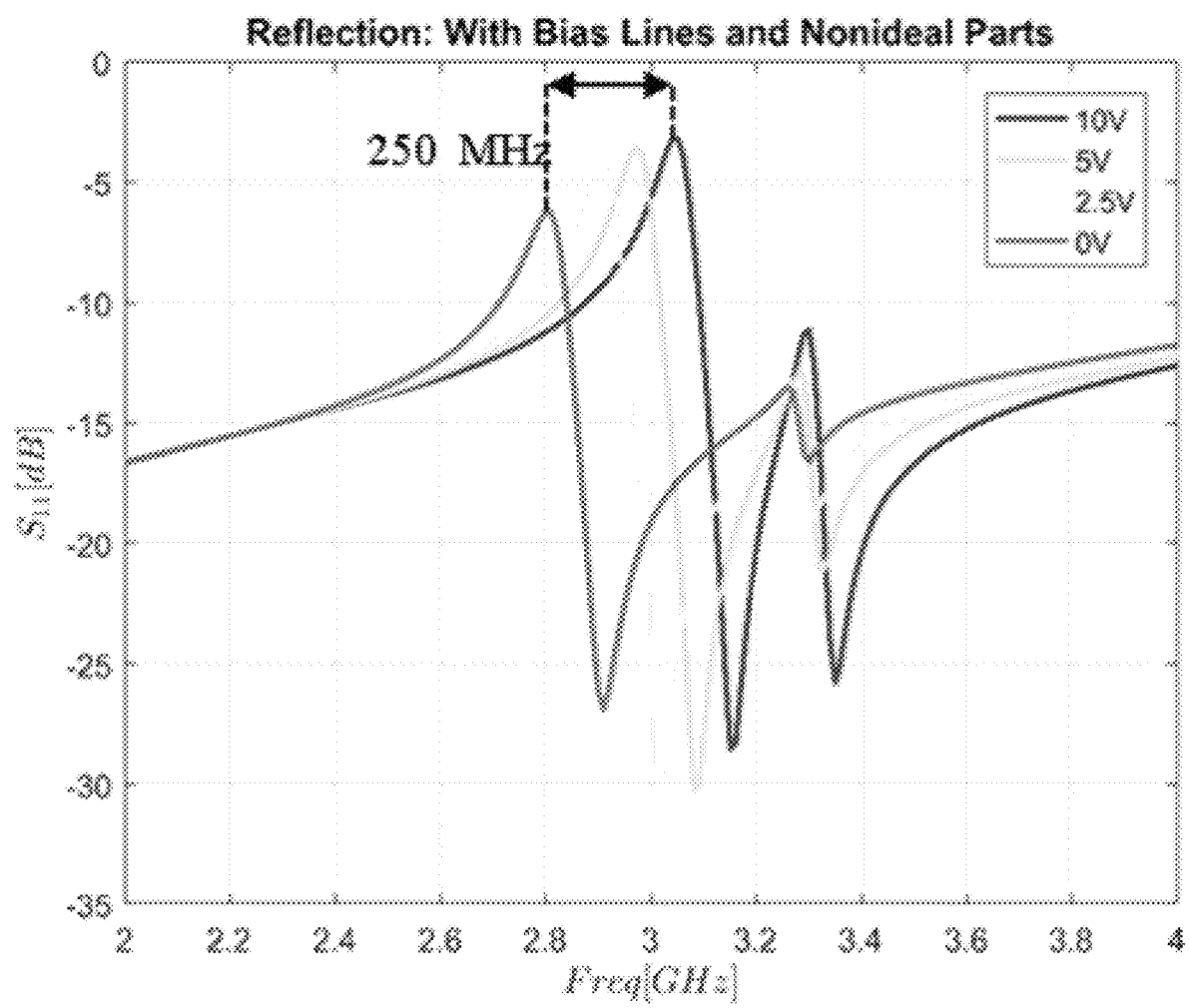
FIG. 9 is a reflection response plot of individual unit cell of the tunable FSS, in accordance with one example of the present invention. Adjusting the biasing voltage from 0 V to 10 V causes the reflection band of the FSS to tune from 2.80 GHz to 3.05 GHz, a total shift of 250 megahertz (MHz).

Another example provides an apparatus for low power chemical sensing, as shown in FIG. 8. The apparatus can comprise a microcontroller configured to receive a voltage signal from a chemical sensor unit, wherein the voltage signal is determined by a concentration of an analyte, as in block 810. The apparatus can comprise a microcontroller configured to transform the voltage signal to an input voltage signal, as in block 820. The apparatus can comprise a microcontroller configured to send the input voltage signal to a plurality of frequency selective surface (FSS) units of an FSS array, wherein the FSS array is configured to communicate a radio frequency (RF) signal in an Institute of Electrical and Electronics Engineers (IEEE) S band with a resonant frequency based on the input voltage to provide the concentration of the analyte, as in block 830.

EXAMPLES

Sensor Card

Nanofibers were fabricated with a self-assembly process and were reactive to classes of chemical analytes or specific analytes. When exposed to the analyte to which it is tuned, a charge transfer process between the nanofiber and the analyte induced a chemo-resistive response. Some nanofibers reacted more strongly than others to a specific analyte and nanofibers would accept or donate charge, depending on the analyte, to affect a net change in conductivity.

The nanofibers were attached to electrodes on substrates that were mounted and wire-bonded to standard printed circuit boards (PCBs). When the nanofiber sensors were excited with a bias voltage and photoenergy, their resistive change produced a current change that converted to a voltage with transimpedance amplification. Sensitivity was controlled with appropriate feedback in the transimpedance circuit to adjust for different conduction efficiencies in different sensors.

Control Board

The control board was designed specifically to perform a low power transformation of high fidelity readings from the sensor card into a voltage bias which could be applied to tune the frequency selective surface (FSS). Because the power budget was a primary concern with the system as a whole, the control board used an ATtiny microcontroller to achieve extremely low power data processing and communication configuration. During typical operation, the system drew current on the order of 200 µA from two CR2032 batteries, allowing for continual operation for several weeks at a time.

Tunable Frequency Selective Surface

A tunable reflecting frequency selective surface was designed to operate near 3 gigahertz (GHz). By applying different voltages across terminals which connect to the control board, the frequency at which the board reflects was changed. This change in frequency was used along with a RADAR system to remotely detect air toxicity found by the detector card since the control board mapped toxin concentration to reflection frequency.

The entire board was approximately 20 centimeters (cm) by 20 cm FSS composed of 400 split ring resonator (SRR) type unit cells. Each unit cell was composed of two nested oppositely-faced copper rings which were connected to each other by a varactor diode and capacitor. Tuning was achieved by varying the reverse biasing voltage on the varactor, which in turn changed its capacitance and thus the resonant frequency of the structure. Biasing was achieved through a pair of copper traces running perpendicular to the assumed polarization of the system. This orientation was chosen to minimize the effect of the bias lines on the reflection response of the system. The bias lines were brought up through the substrate and connected, with choke inductors to the rings.

The system was simulated using high-frequency structure simulator (HFSS) with the component impedances first modeled in advanced design system (ADS). Parts were selected with manufacturing in mind while still maximizing the tuning range and reflection magnitude of the FSS. The unit cell was simulated assuming periodic boundary conditions, which correspond to an infinite array of unit cells. The reflection response for this set up, shown in FIG. 9, demonstrated effective tuning across a 250 megahertz (MHz) band centered just below 3 GHz. All peaks reach well above −10 decibels (dB), a reasonable reflection magnitude where the FSS would be detectable. In addition to a wide tuning band, the high Q-factor of the peaks for different voltage values guarantees a continuous usable tuning range.

Validation was done to model the sensor system in finite array form. The results shown above are reflective of the system in an idealized infinitely periodic environment. However, the actual system can be a finite array of 400 elements, and so a more realistic finite array case was simulated before moving on to a fabrication stage. While the performance of the finite array can no doubt be slightly degraded relative to what has been shown, it was expected to still achieve the desired performance due to the size of the final FSS board.

Receiver Horn

A 725 (25×29 element) FSS array was positioned near a receiver horn. The horn was a pyramidal antenna design and was used to interrogate the FSS. An Agilent E5071C network analyzer with 100 kilohertz (kHz) to 8.5 gigahertz (GHz) bandwidth was used to read the horn antenna output. A one port calibration was performed with Agilent's Cal Kit 85032F using open, short, and 50 ohm loads on the far end of the input cable before it was attached to the horn. The horn was then connected to the analyzer, its signal was optimized, and its position locked.

The sensor card, inserted in the control card, was inside the acrylic gas delivery chamber, lower left corner. The chamber had an interior volume of 48.9 cm×31.8 cm×12.1 cm=18,816 $cm^3$ (18.8 L). Two different light-emitting diode (LED) boards were used in the analysis, mounted on the outside of the chamber ~3 cm directly in front of the sensor card. The low intensity LEDs were ~3500 LUX at the sensor; the high intensity LEDs were ~160,000 LUX at the sensor. The external LED was used to photoexcite the sensors (i.e. it is noted that some nanofibers respond more effectively to binding with analytes when illuminated).

One sensor, VAP-025, was investigated. When exposed to varying concentrations of ammonia, the sensor current, converted to a voltage, ranged from 0 to 2 volts (V), was digitized by a 20 bit delta-sigma analog-to-digital converter (ADC). Serial (SPI) signals from the ADC were input to the control card. An ATTiny microprocessor on the control card read the ADC voltage and output pulse width modulated (PWM) signals to a charge storage capacitor and filter that multiplied the ADC output by five to give a range of 0 to 10 V to the FSS.

Figure 10B:
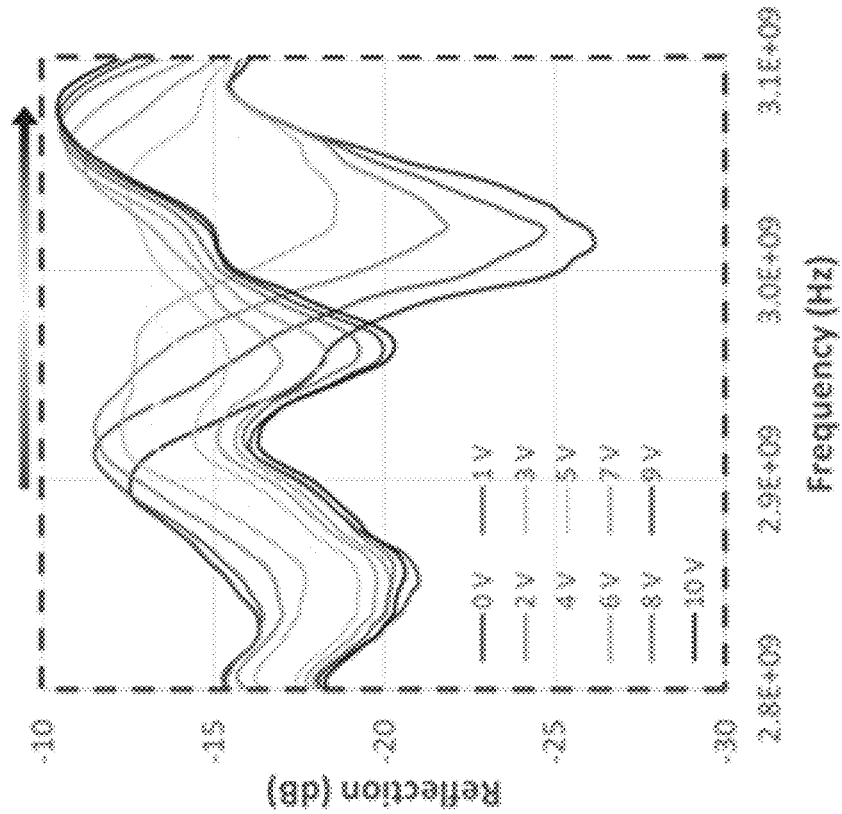
FIGS. 10A-10C are FSS reflectance spectra collected at different voltages, in accordance with one example of the present invention.
Figure 10A:
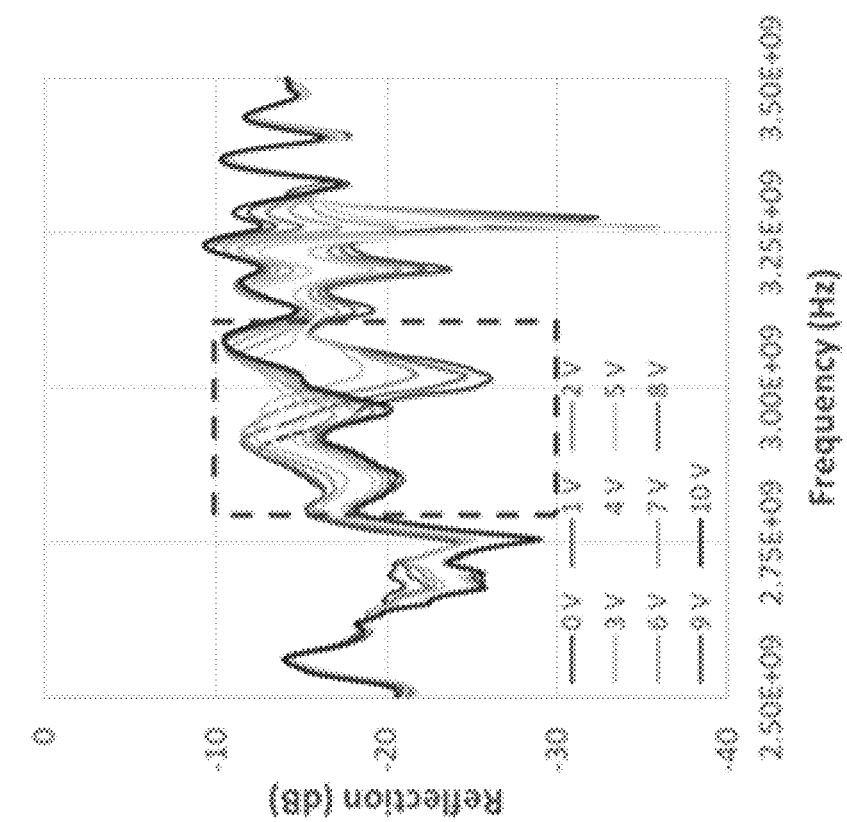
Figure 11A:
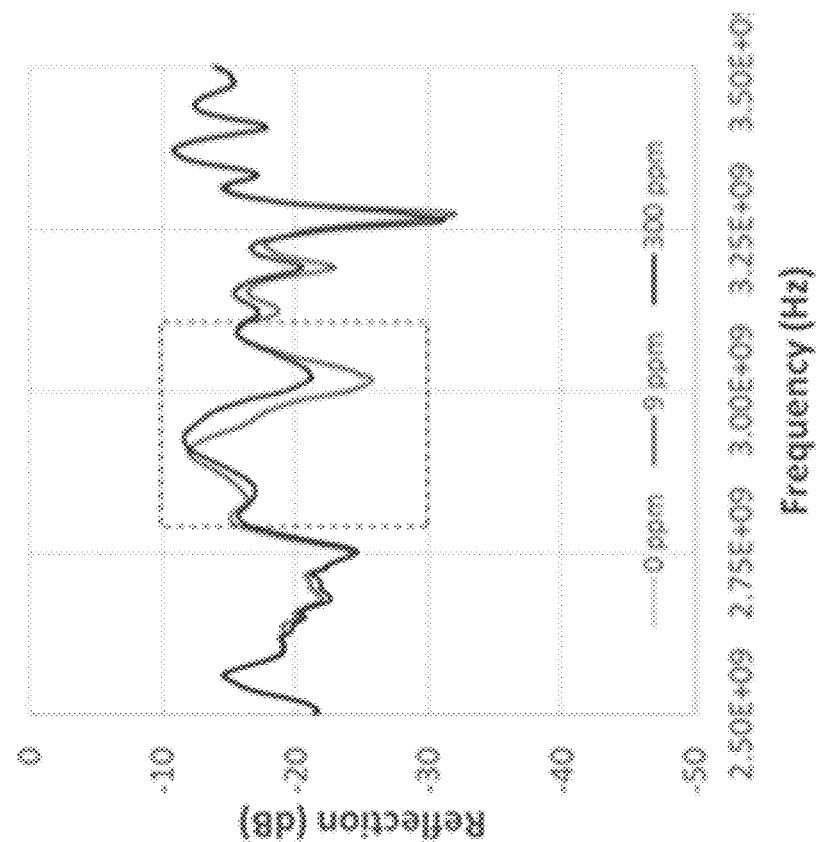
Figure 10C:
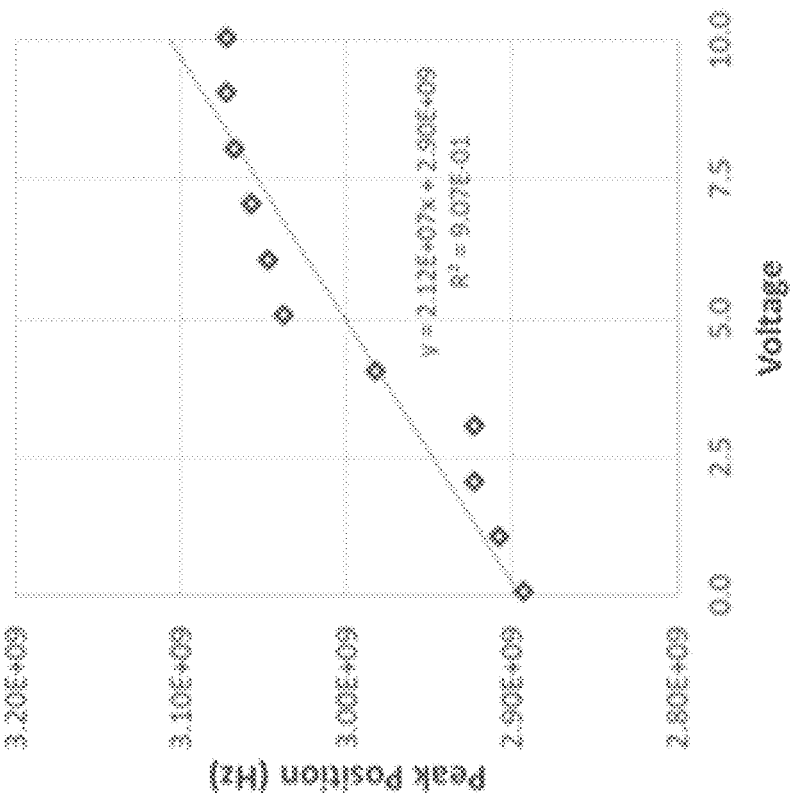
Figures 11B, 11C:
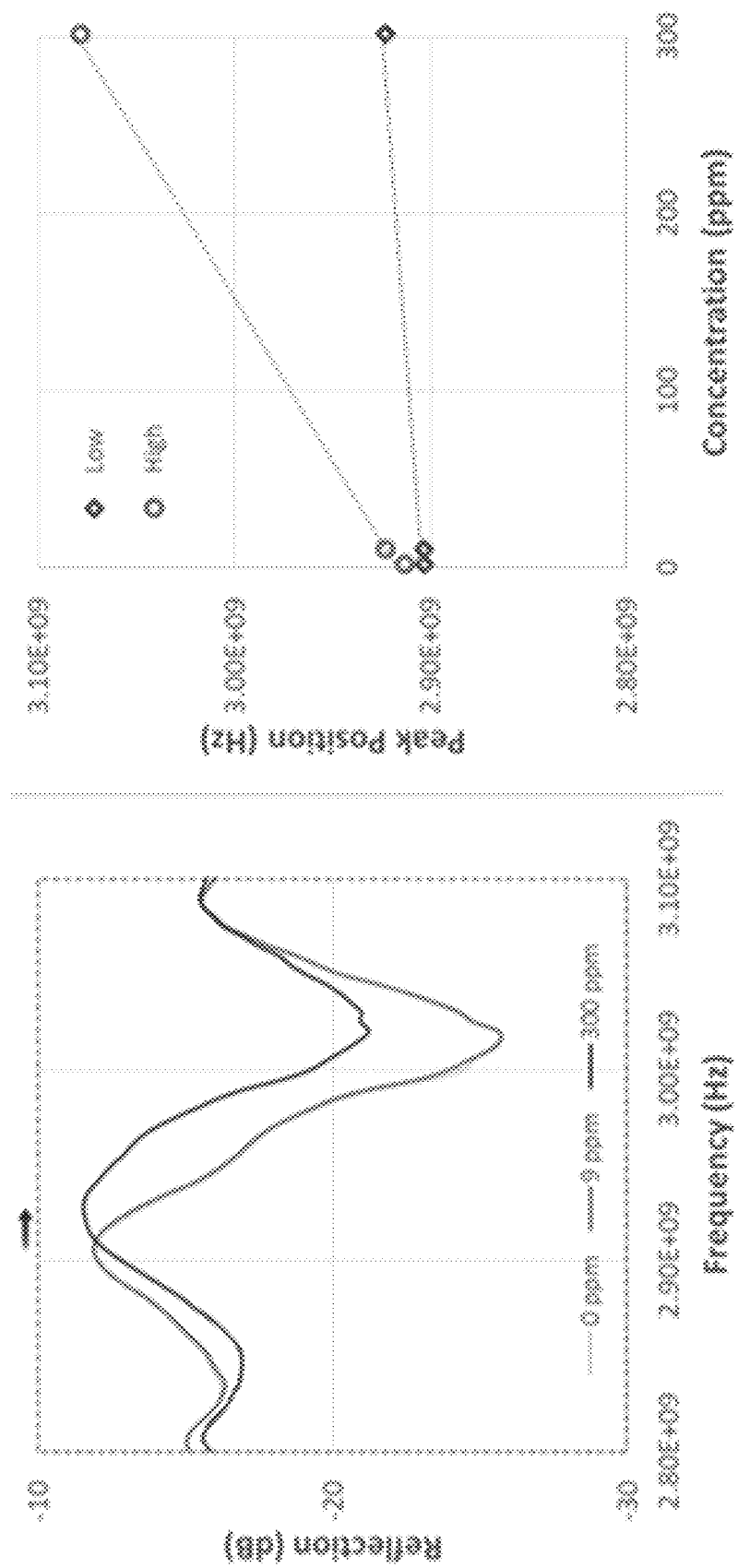
Figures 11D, 11E:
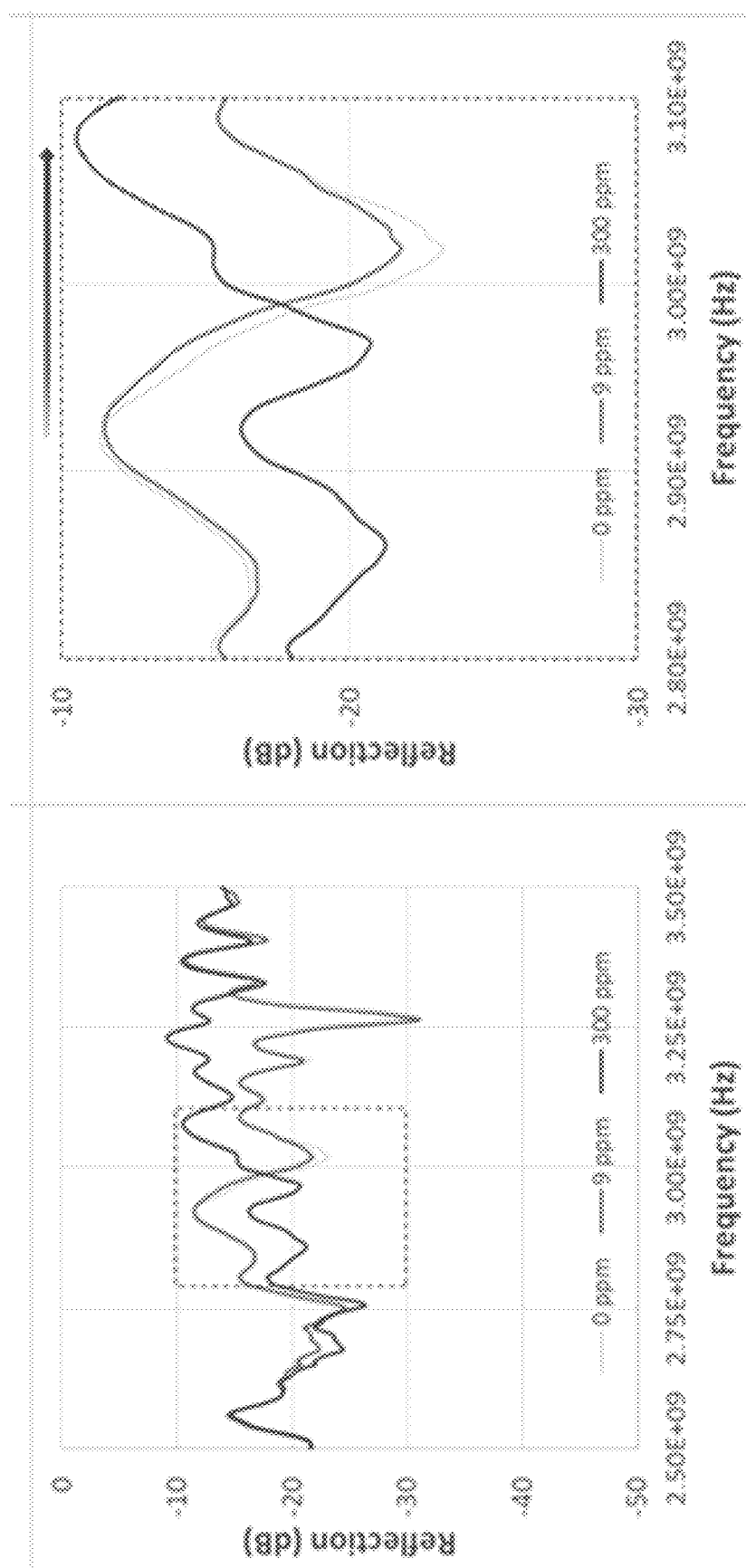
FIGS. 11D-11F are sensor response data measured from the FSS, in accordance with one example of the present invention.
Figure 11F:
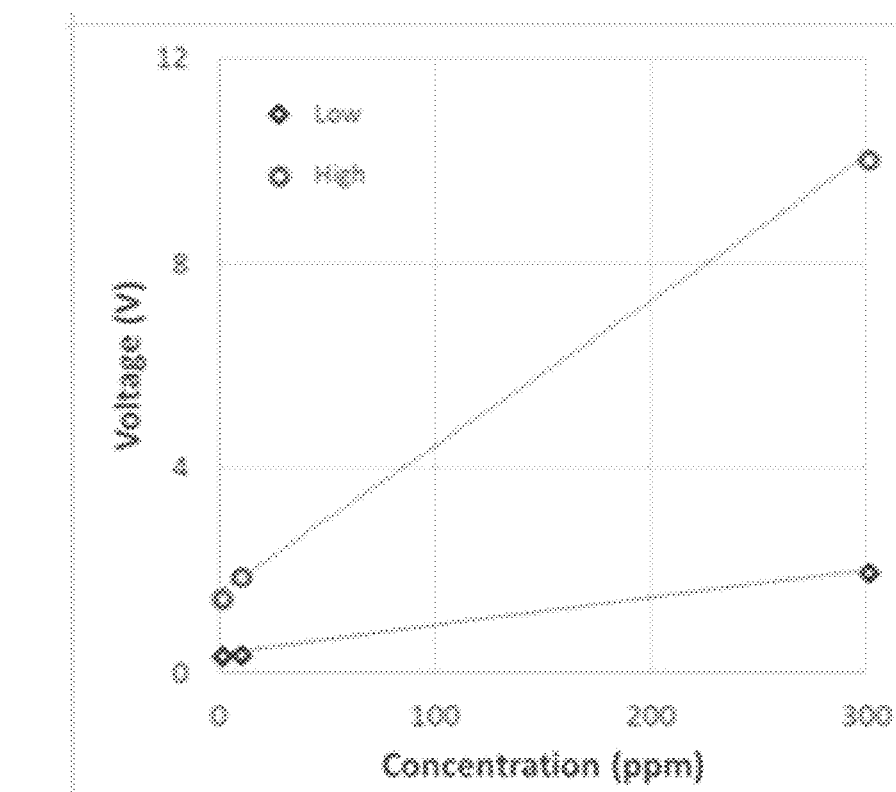

Table 1 shows the peak frequency transmitted by the FSS array from the voltage input. In the laboratory, space constraints and proximity to gas delivery dictated FSS placement. Without an anechoic or Faraday environment, spurious reflections were evident after calibration. However, even in this real-world environment, frequency peaks for low ammonia concentration compared to high ammonia concentration showed peak heights of at least 3 dB. FIGS. 10A-10C show the reflectance spectra of ten voltages and a summary of the shift in peak location.

TABLE 1

Frequency peak marked on network spectrum by voltage. Absolute dB is amplitude of the peak.

| Volts | Frequency GHz | Absolute dB |
| --- | --- | --- |
| 0 | 2.8901 | −10.38 |
| 1 | 2.8977 | −10.32 |
| 2 | 2.9371 | −10.59 |
| 3 | 2.9498 | −10.62 |
| 4 | 3.0032 | −11.31 |
| 5 | 3.0133 | −10.90 |
| 6 | 3.0591 | −10.75 |
| 7 | 3.0654 | −9.76 |
| 8 | 3.0693 | −9.35 |
| 9 | 3.0743 | −9.32 |
| 10 | 3.0769 | −9.33 |

To test the sensors, ammonia was delivered at concentrations relevant to health and safety. Permissible exposure limit (PEL), 50 ppm, could not be tested because it fell within a capability gap so 9 ppm was tested instead. A second concentration, 300 ppm, is considered immediately dangerous to life and health (IDLH). Two different light intensities were used to evaluate the impact of illumination on sensor response. The results are presented in Table 2 and FIGS. 11A-11F. Overall, illumination intensity played a major role. With low light intensity, PEL was indistinguishable from no ammonia. However, it was resolved under higher illumination. As a general guideline, illumination can often range from about 0 to 500 lumens, and in some cases from 10 to 450 lumens.

TABLE 2

Voltage response to two levels of NH3 concentration at two LED Intensities.

| | 0 ppm | 9 ppm | 300 ppm |
| --- | --- | --- | --- |
| Low Illumination | 400 mV | 415 mV | 2,030 mV |
| High Illumination | 1,500 mV | 1,950 mV | 10,100 mV |

Non-Ideal Unit Cell Model

Figure 12:
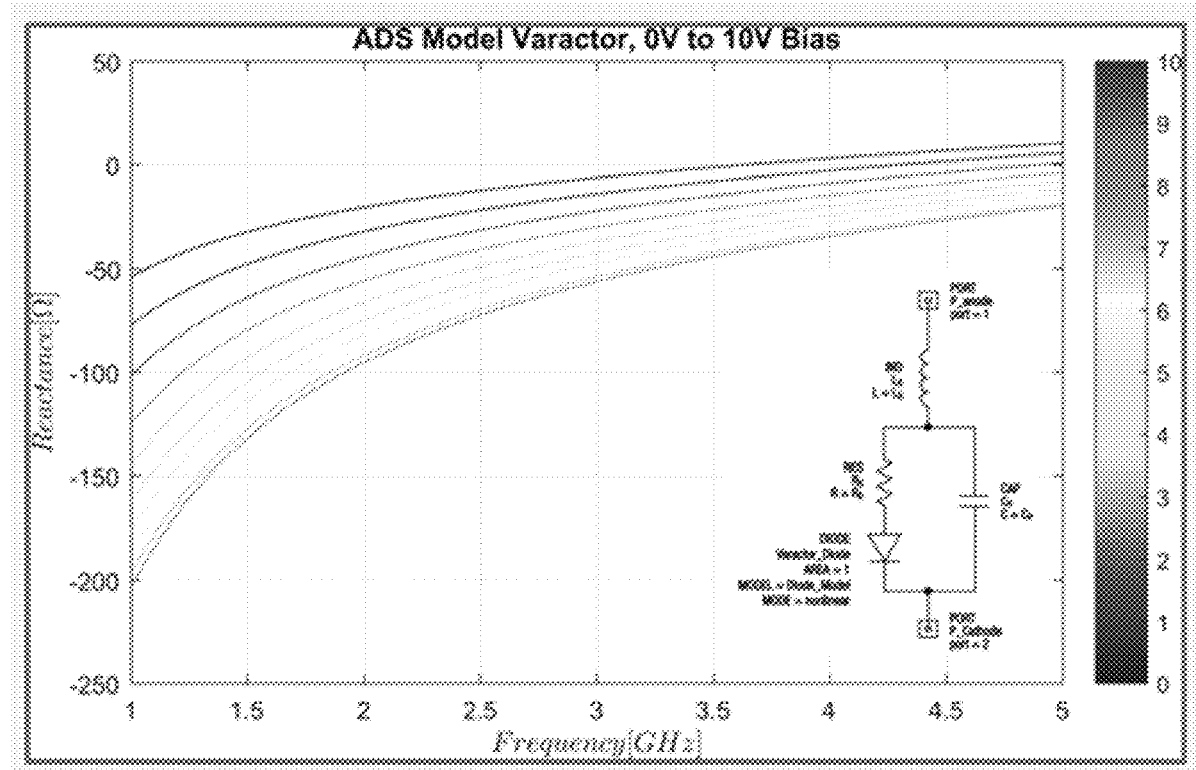
FIG. 12 is a graph of selected varactor modeled in ADS software, in accordance with one example of the present invention.

A selected non-ideal varactor was modeled using ADS software, as illustrated in FIG. 12. The graph shows the reactance as a function of frequency in GHz. Reactance tuning was observed as the biasing voltage was adjusted from 0 V to 10 V. The varactor resistance was observed to be small (e.g., about 0.5 ohms).

Figure 13:
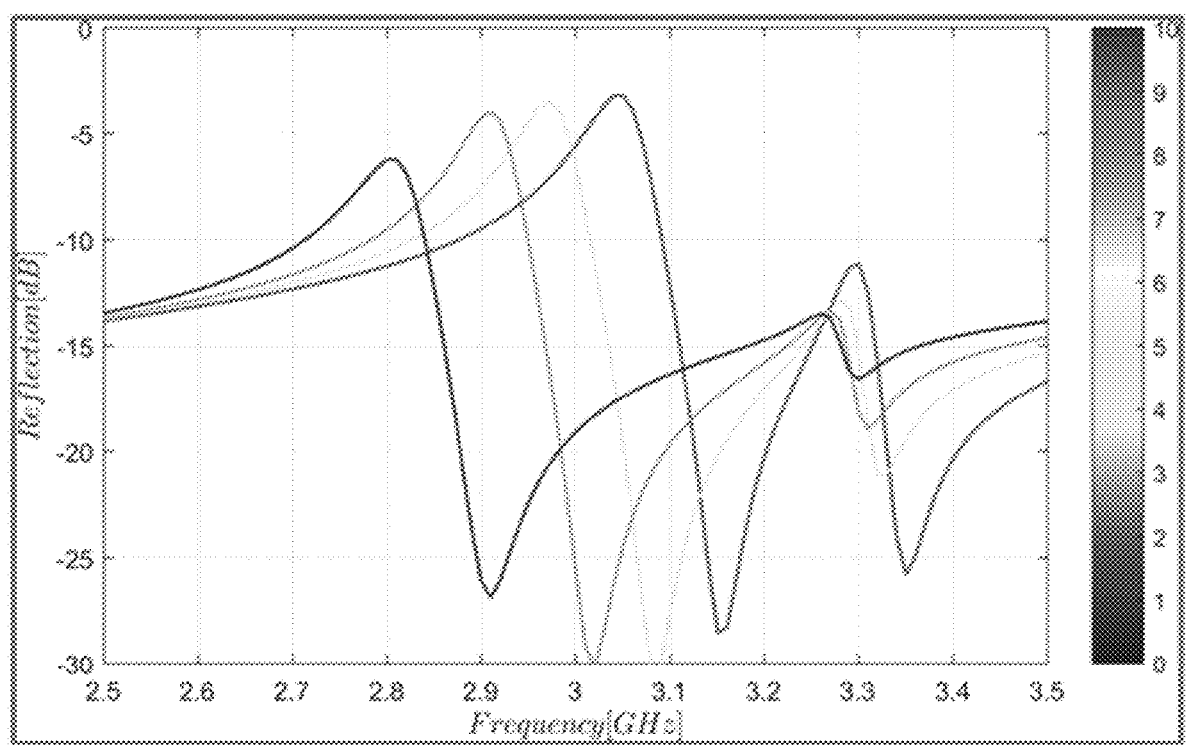
FIG. 13 is a graph modeled and simulated using non-ideal parts in HFSS, in accordance with one example of the present invention.
Figure 14:
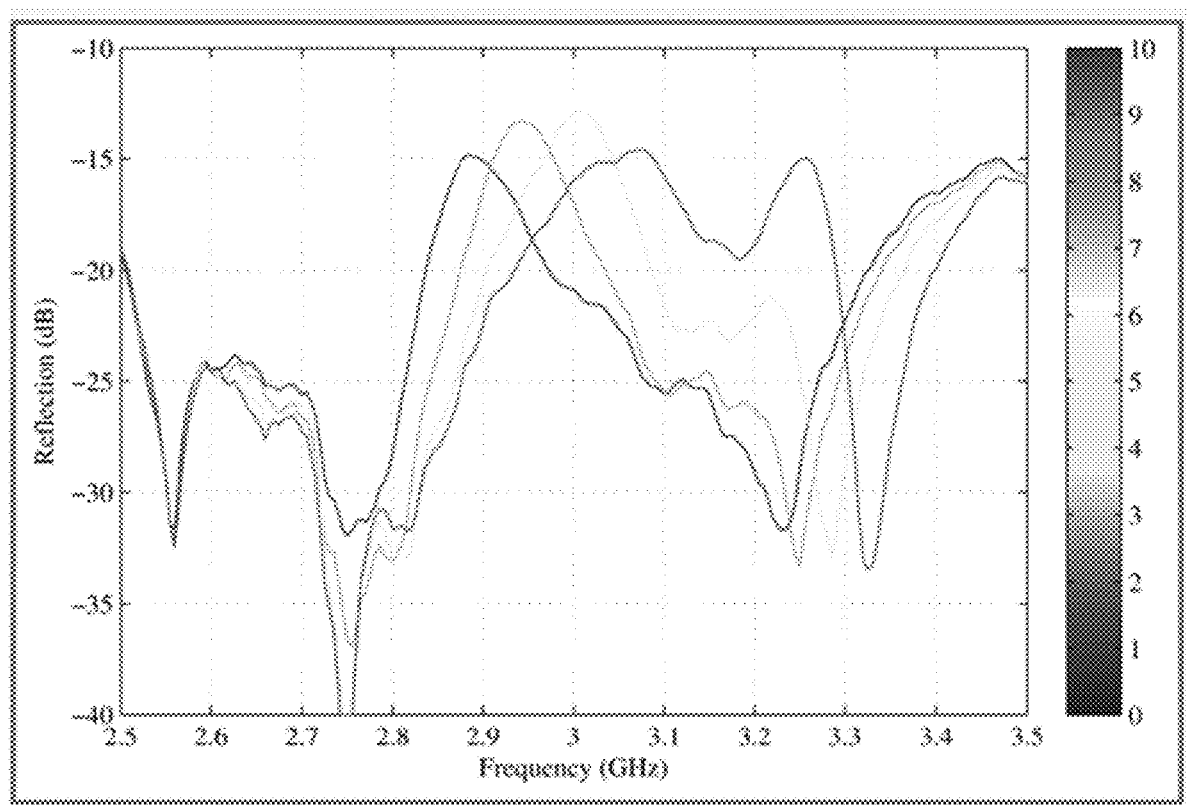
FIG. 14 is a graph of measurements taken with the VNA that confirm tuning as predicted in the infinite array simulation, in accordance with one example of the present invention.

A selected non-ideal unit cell was modeled and simulated using non-ideal parts in HFSS. The results of the simulation predict a 250 MHz frequency shift from a 0V peak to a 10 V peak that was centered around 3 GHz, as illustrated in FIG. 13.

Isolated FSS Panel Testing

Measurements were taken with a vector network analyzer (VNA) that confirmed tuning as predicted in the infinite array simulation, as illustrated in FIG. 15. The measurements show a 195 MHz frequency shift from a 0 V peak to a 10 V peak that was centered around 3 GHz. The measurements were gathered based on a truncated panel size of about 2.5λ×2.5λ in size, ferrite bead isolation bias network, and additional acrylic sheets for chemical isolation.

Isolated FSS testing was setup using a WR-284 waveguide feeding a custom-built 10-dB standard horn for excitation. The FSS panel was housed inside the acrylic box in anticipation of live chemical testing. Tuning was observed as the bias voltage varied from 0 V to 10 V. The size of the testing panel was 25×25 unit cells, or about 26.5 centimeters (cm)×26.5 cm.

Nanofiber Sensors

Nanofibers can be used to sense different toxin concentrations that allow for highly compact and low power electronic sensor form factor. Integrated with FSS through custom-designed and professionally fabricated control board which is powered with lithium (Li)-ion CR2032 coin batteries. The fully integrated system was application tested with ammonia inside an acrylic chamber.

Ammonia Exposure Test

One sensor was tested against ammonia, for a concentration of 9 parts per million (ppm) (which is near the permissible exposure limit (PEL)/recommended exposure limit (REL)) and 300 ppm (which is near the immediately dangerous to life or health (IDLH) limit). Two laser intensities were used to study the impact. The sensors were photoactivated or the sensors were configured to perform in the dark.

Figures 15A, 15B:
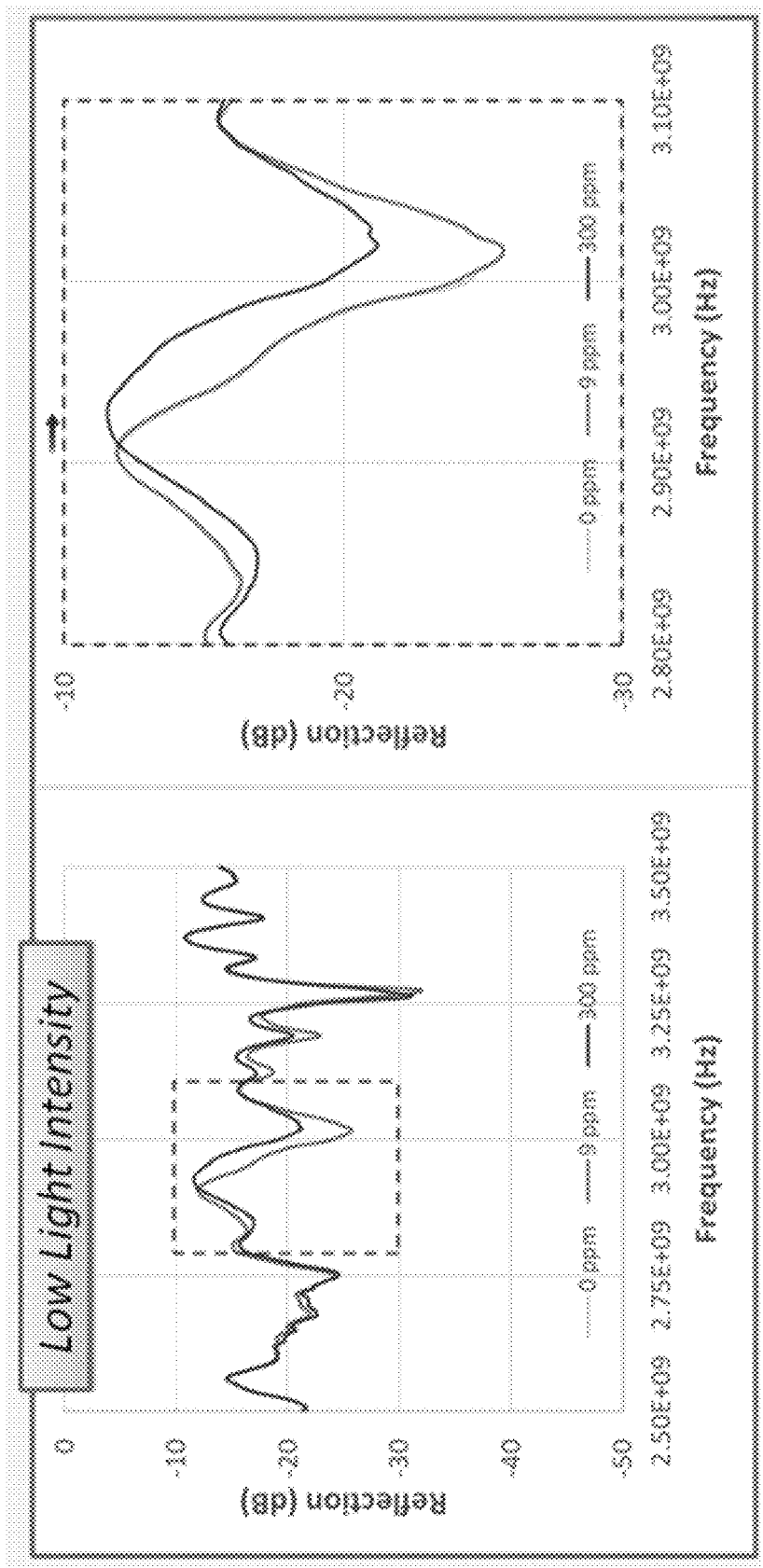
FIG. 15A is a graph of reflection magnitude for a range of frequencies in a low light intensity, in accordance with one example of the present invention.
FIG. 15B is a zoomed in spectra of the region of interest for three concentrations of ammonia under low illumination intensities.
Figures 16A, 16B:
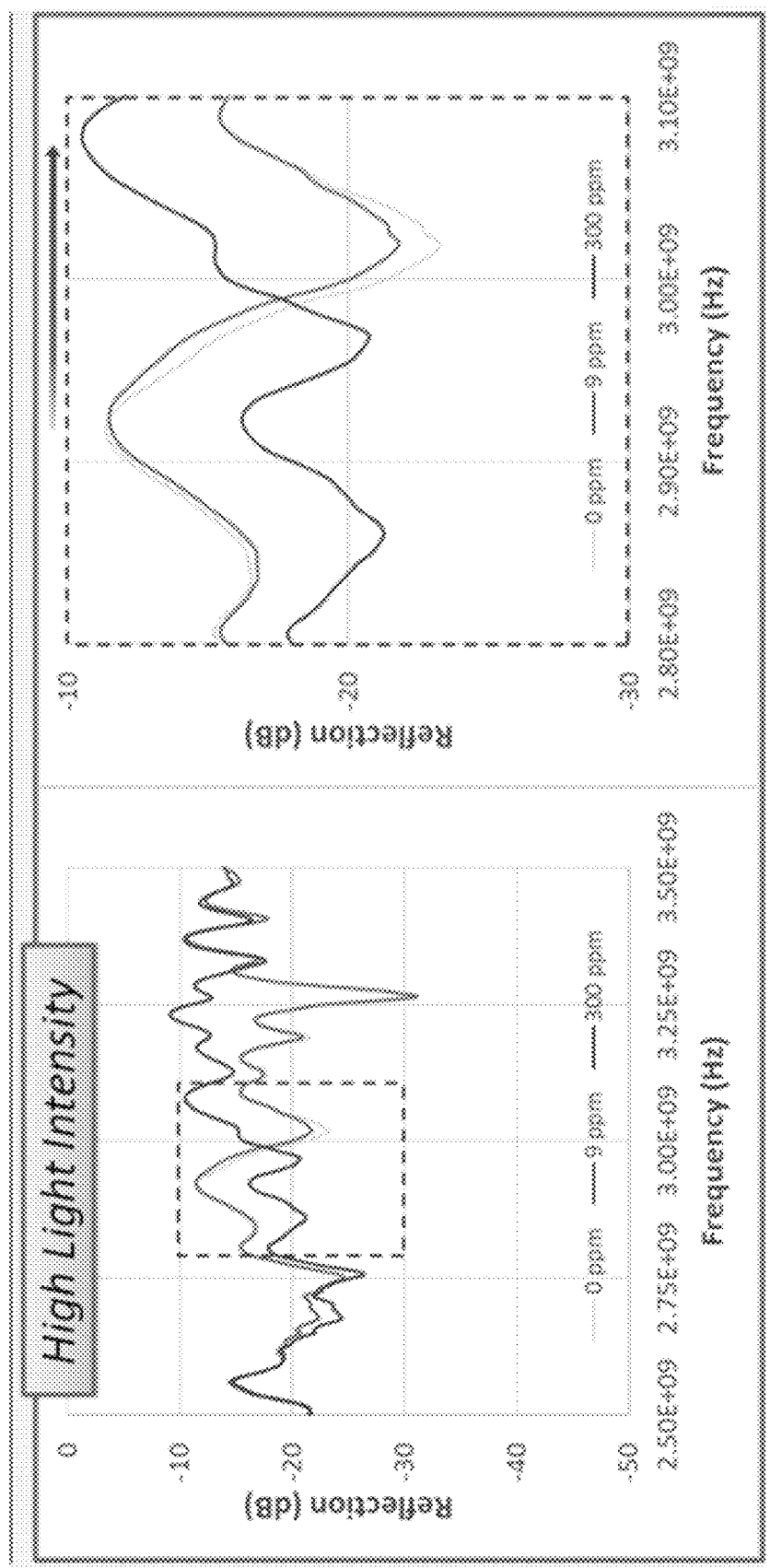
FIG. 16A is a graph of reflection magnitude for a range of frequencies in high light intensity, in accordance with one example of the present invention.
FIG. 16B is a zoomed in spectra of the region of interest for three concentrations of ammonia under high illumination intensities.

The results for low light intensity are shown in FIGS. 15A and 15B for a frequency range between 2.5 GHz and 3.5 GHz and for a frequency range between 2.8 GHz and 3.1 GHz. The results for high light intensity are shown in FIGS. 16A and 16B for a frequency range between 2.5 GHz and 3.5 GHz and for a frequency range between 2.8 GHz and 3.1 GHz. The control board firmware can be modified to logarithmically scale the voltage to improve response differentiation at low toxin concentrations.

The foregoing detailed description describes the invention with reference to specific exemplary embodiments. However, it will be appreciated that various modifications and changes can be made without departing from the scope of the present invention as set forth in the appended claims. The detailed description and accompanying drawings are to be regarded as merely illustrative, rather than as restrictive, and all such modifications or changes, if any, are intended to fall within the scope of the present invention as described and set forth herein.

What is claimed is:

1. A system for low power chemical sensing, comprising:
a voltage shift unit configured to:
receive a voltage signal from a chemical sensor unit, wherein the voltage signal is determined by a concentration of an analyte;
transform the voltage signal to an input voltage signal;
send the input voltage signal to a plurality of frequency selective surface (FSS) units of an FSS array;
the FSS array comprising:
the plurality of FSS units, wherein each FSS unit comprises:
a first nested split ring resonator (SRR) configured to receive a first voltage from the input voltage signal via a first bias line;
a second nested SRR configured to receive a second voltage from the input voltage signal via a second bias line; and
a variable capacitance unit coupled to the first nested SRR and the second nested SRR, wherein the variable capacitance unit is configured to convert a voltage bias from the first bias line and the second bias line to a capacitance; and
wherein the FSS array is configured to produce a radio frequency (RF) signal in an Institute of Electrical and Electronics Engineers (IEEE) S band for communication to an RF receiver; and
the RF receiver configured to:
receive the RF signal in the S band;
identify a resonant frequency from a peak reflection magnitude from the RF signal; and
determine the concentration of the analyte based on the resonant frequency.

2. The system of claim 1, wherein the chemical sensor unit further comprises a nanofiber sensor configured to change conductivity based on the concentration of the analyte, wherein the nanofiber sensor is activated by exposure to light.

3. The system of claim 1, wherein the chemical sensor unit further comprises:
a nanofiber sensor comprised of nanofibers formed from perylene tetracarboxylic diimide molecules.

4. The system of claim 1, wherein the voltage shift unit is a microcontroller which is further configured to:
select a value of the input voltage signal to determine the resonant frequency, wherein the value of the input voltage signal is based on a mapping between the concentration of the analyte and the resonant frequency.

5. The system of claim 4, wherein the microcontroller is further configured to:
identify a first threshold value for the voltage signal received from the chemical sensor unit; and
identify a second threshold value for the voltage signal received from the chemical sensor unit,
wherein a value for the voltage signal between the first threshold value and the second threshold value indicates that the concentration of the analyte is in a permissible exposure limit (PEL) range, and
wherein the value for the voltage signal higher than the second threshold value indicates that the concentration of the analyte is in an immediately dangerous to life or health (IDHL) range.

6. The system of claim 1, wherein the voltage shift unit is at least one amplifier and at least one level shifter, or an increased bias voltage applied to the chemical sensor unit.

7. The system of claim 1, wherein the FSS array further comprises:
a first choke inductor coupled between the first bias line and the first nested SRR; and
a second choke inductor coupled between the second bias line and the second nested SRR,
wherein at least one of the first choke inductor and the second choke inductor is configured to isolate at least one of the first bias line and the second bias line over an operating bandwidth.

8. The system of claim 1, wherein at least one of the first bias line and the second bias line is perpendicular to a field polarization and the variable capacitance unit is a varactor.

9. The system of claim 1, wherein the FSS array is further configured to:
produce the RF signal in an operating bandwidth of the IEEE S band for communication to the RF receiver, wherein the operating bandwidth includes a frequency range between 2.80 gigahertz (GHz) and 3.05 GHz.

10. The system of claim 1, wherein the plurality of FSS units includes a number of FSS units configured to produce the RF signal with a signal-to-noise ratio (SNR) greater than a selected threshold.

11. The system of claim 1, wherein the FSS array is further configured to produce radio detection and ranging (RADAR) identifiable reflection band tuning.

12. The system of claim 1, wherein the RF receiver is further configured to:
identify that the concentration of the analyte is in a permissible exposure limit (PEL) range or an immediately dangerous to life or health (IDHL) range.

13. The system of claim 1, further comprising a control board configured to:
power the chemical sensor unit from a power source;
power the microcontroller from the power source; and
power the FSS array from the power source, wherein the power source is configured to provide a total current of less than 250 microamperes ($\mu A$).

14. A method for low power chemical sensing, comprising:
receiving, at a microcontroller from a chemical sensor unit, a voltage signal determined by a concentration of an analyte;
sending, at the microcontroller to a plurality of frequency selective surface (FSS) units of an FSS array, an input voltage signal determined using the voltage signal from the chemical sensor unit;
communicating, from the FSS array to a radio frequency (RF) receiver, an RF signal in an Institute of Electrical and Electronics Engineers (IEEE) S band with a resonant frequency, wherein the RF signal is determined using the input voltage signal; and
determining, at the RF receiver, the concentration of the analyte based on the resonant frequency.

15. The method of claim 14, further comprising:
selecting, at the microcontroller, a value of the input voltage signal to determine the resonant frequency, wherein the value of the input voltage signal is based on a mapping between the concentration of the analyte and the resonant frequency.

16. The method of claim 14, further comprising:
identifying, at the microcontroller, a first threshold value for the voltage signal received from the chemical sensor unit; and
identifying, at the microcontroller, a second threshold value for the voltage signal received from the chemical sensor unit,
wherein a value for the voltage signal between the first threshold value and the second threshold value indicates that the concentration of the analyte is in a permissible exposure limit (PEL) range, and
wherein the value for the voltage signal higher than the second threshold value indicates that the concentration of the analyte is in an immediately dangerous to life or health (IDHL) range.

17. The method of claim 14, further comprising:
producing, at the FSS array, the RF signal in an operating bandwidth of the IEEE S band for communication to the RF receiver, wherein the operating bandwidth includes a frequency range between 2.80 gigahertz (GHz) and 3.05 GHz.

18. The method of claim 14, further comprising:
producing, at the FSS array, the RF signal with a signal-to-noise ratio (SNR) greater than a selected threshold.

19. The method of claim 14, further comprising:
powering the chemical sensor unit from a power source;
powering the microcontroller from the power source; and
powering the FSS array from the power source, wherein the power source is configured to provide a total current of less than 250 microamperes ($\mu$A).

20. An apparatus for low power chemical sensing, comprising a voltage shift unit configured to:
receive a voltage signal from a chemical sensor unit, wherein the voltage signal is determined by a concentration of an analyte;
transform the voltage signal to an input voltage signal; and
send the input voltage signal to a plurality of frequency selective surface (FSS) units of an FSS array, wherein the FSS array is configured to communicate a radio frequency (RF) signal in an Institute of Electrical and Electronics Engineers (IEEE) S band with a resonant frequency based on the input voltage to provide the concentration of the analyte.

21. The apparatus of claim 20, wherein the voltage shift unit is a microcontroller further configured to:
select a value of the input voltage signal to determine the resonant frequency, wherein the value of the input voltage signal is based on a mapping between the concentration of the analyte and the resonant frequency.

22. The apparatus of claim 21, wherein the microcontroller is further configured to:
identify a first threshold value for the voltage signal received from the chemical sensor unit; and
identify a second threshold value for the voltage signal received from the chemical sensor unit,
wherein a value for the voltage signal between the first threshold value and the second threshold value indicates that the concentration of the analyte is in a permissible exposure limit (PEL) range, and
wherein the value for the voltage signal higher than the second threshold value indicates that the concentration of the analyte is in an immediately dangerous to life or health (IDHL) range.

* * * * *